United States Patent
Lewis et al.

(10) Patent No.: US 10,117,968 B2
(45) Date of Patent: Nov. 6, 2018

(54) METHOD OF PRINTING A TISSUE CONSTRUCT WITH EMBEDDED VASCULATURE

(71) Applicant: President and Fellows of Harvard College, Cambridge, MA (US)

(72) Inventors: Jennifer A. Lewis, Cambridge, MA (US); David B. Kolesky, Cambridge, MA (US); Mark A. Skylar-Scott, Brookline, MA (US); Kimberly A. Homan, Somerville, MA (US); Ryan L. Truby, Boston, MA (US); Amelia Sydney Gladman, Cambridge, MA (US)

(73) Assignee: President And Fellows Of Harvard College, Cambridge, MA (US)

( * ) Notice: Subject to any disclaimer, the term of this patent is extended or adjusted under 35 U.S.C. 154(b) by 0 days.

(21) Appl. No.: 15/146,613

(22) PCT Filed: Nov. 4, 2014

(86) PCT No.: PCT/US2014/063810
§ 371 (c)(1),
(2) Date: May 4, 2016

(87) PCT Pub. No.: WO2015/069619
PCT Pub. Date: May 14, 2015

(65) Prior Publication Data
US 2016/0287756 A1    Oct. 6, 2016

Related U.S. Application Data

(60) Provisional application No. 61/900,029, filed on Nov. 5, 2013.

(51) Int. Cl.
| | |
|---|---|
| *A61L 27/50* | (2006.01) |
| *B29C 64/40* | (2017.01) |
| *B29C 64/106* | (2017.01) |
| *A61L 27/38* | (2006.01) |
| *B33Y 10/00* | (2015.01) |
| *B33Y 80/00* | (2015.01) |
| *A61F 2/06* | (2013.01) |
| *A61L 27/22* | (2006.01) |
| *A61F 2/10* | (2006.01) |
| *A61L 27/36* | (2006.01) |
| *C12M 1/26* | (2006.01) |

(52) U.S. Cl.
CPC ............ *A61L 27/507* (2013.01); *A61F 2/06* (2013.01); *A61F 2/105* (2013.01); *A61L 27/222* (2013.01); *A61L 27/225* (2013.01); *A61L 27/3633* (2013.01); *A61L 27/3808* (2013.01); *A61L 27/3813* (2013.01); *A61L 27/3826* (2013.01); *B29C 64/106* (2017.08); *B29C 64/40* (2017.08); *B33Y 10/00* (2014.12); *B33Y 80/00* (2014.12); *A61F 2240/002* (2013.01); *A61L 2430/34* (2013.01); *C12M 33/00* (2013.01)

(58) Field of Classification Search
None
See application file for complete search history.

(56) References Cited

U.S. PATENT DOCUMENTS

| | | |
|---|---|---|
| 5,827,641 A | 10/1998 | Parenteau et al. |
| 7,053,125 B2 | 5/2006 | Lewis et al. |
| 7,141,617 B2 | 11/2006 | Gratson et al. |
| 7,790,061 B2 | 9/2010 | Gratson et al. |
| 7,799,251 B2 | 9/2010 | Therriault et al. |
| 7,922,939 B2 | 4/2011 | Lewis et al. |

(Continued)

FOREIGN PATENT DOCUMENTS

| | | |
|---|---|---|
| JP | 2012-120696 A | 6/2012 |
| WO | WO 2013/006399 A2 | 1/2013 |

(Continued)

OTHER PUBLICATIONS

Hansen et al., Self-Healing Materials with Interpenetrating Microvascular Networks, Adv. Mater. 2009, 21, pp. 1-5.*
International Preliminary Report received in PCT Application No. PCT/US2014/063810 dated May 10, 2016.
International Search Report and Written Opinion received in PCT Application No. PCT/US2014/063810 dated Feb. 18, 2015.
Ahn, Bok Y. et al., "Omnidirectional Printing of Flexible, Stretchable, and Spanning Silver Microelectrodes," *Science*, 323 (2009) pp. 1590-1593.

(Continued)

*Primary Examiner* — Renee Claytor
*Assistant Examiner* — Srikanth Patury
(74) *Attorney, Agent, or Firm* — Brinks Gilson & Lione

(57) ABSTRACT

A printed tissue construct comprises one or more tissue patterns, where each tissue pattern comprises a plurality of viable cells of one or more predetermined cell types. A network of vascular channels interpenetrates the one or more tissue patterns. An extracellular matrix composition at least partially surrounds the one or more tissue patterns and the network of vascular channels. A method of printing a tissue construct with embedded vasculature comprises depositing one or more cell-laden filaments, each comprising a plurality of viable cells, on a substrate to form one or more tissue patterns. Each of the one or more tissue patterns comprises one or more predetermined cell types. One or more sacrificial filaments, each comprising a fugitive ink, are deposited on the substrate to form a vascular pattern interpenetrating the one or more tissue patterns. The vascular pattern and the one or more tissue patterns are at least partially surrounded with an extracellular matrix composition. The fugitive ink is then removed to create vascular channels in the extracellular matrix composition, thereby forming an interpenetrating vascular network in a tissue construct.

11 Claims, 21 Drawing Sheets

(56) References Cited

U.S. PATENT DOCUMENTS

| | | |
|---|---|---|
| 7,956,102 B2 | 6/2011 | Lewis et al. |
| 8,101,139 B2 | 1/2012 | Therriault et al. |
| 8,187,500 B2 | 5/2012 | Lewis et al. |
| 2010/0330220 A1 | 12/2010 | Gratson et al. |
| 2011/0270412 A1 | 11/2011 | Bellan et al. |
| 2012/0058174 A1 | 3/2012 | West et al. |
| 2012/0089238 A1 | 4/2012 | Hyun-Wook et al. |
| 2013/0084449 A1 | 4/2013 | Lewis et al. |
| 2014/0314954 A1 | 10/2014 | Lewis et al. |

FOREIGN PATENT DOCUMENTS

| | | |
|---|---|---|
| WO | WO 2013/040078 A2 | 3/2013 |
| WO | WO 2013/096664 A1 | 6/2013 |
| WO | WO 2014/182535 A1 | 11/2014 |
| WO | WO 2014/209994 A2 | 12/2014 |
| WO | WO 2015/069619 A1 | 5/2015 |
| WO | WO 2015/073944 A2 | 5/2015 |
| WO | WO 2015/120429 A1 | 8/2015 |
| WO | WO 2015/120430 A1 | 8/2015 |

OTHER PUBLICATIONS

Gratson, Gregory M. et al. "Direct Writing of Three-Dimensional Webs," *Nature*, 428 (2004) p. 386.

Lewis, Jennifer A., "Colloidal Processing of Ceramics," *Journal of the American Ceramic Society*, 83, 10 (2000) pp. 2341-2359.

Lewis, Jennifer A. "Direct Ink Writing of 3D Functional Materials," *Adv. Funct. Mater.*, 16 (2006) pp. 2193-2204.

Therriault, Daniel et al., "Rheological Behavior of Fugitive Organic Inks for Direct-Write Assembly," *Applied Rheology*, 17, 1 (2007) pp. 10112-1-10112-8.

Wu, Willie, et al., "Omnidirectional Printing of 3D Microvascular Networks," *Advanced Materials*, 23, 24 (2011) pp. H178-H183.

Reporting letter dated Jun. 29, 2017 received in Singapore Application No. 11201603543W with Search Report dated May 24, 2016 and Written Opinion dated Jun. 12, 2017.

Lee, et al., "On-Demand Three-Dimensional Freeform Fabrication of Multi-Layered Hydrogel Scaffold With Fluidic Channels," *Biotechnology and Bioengineering*, 105(6):1178-1186 (Apr. 15, 2010).

Miller, et al., "Rapid Casting of Patterned Vascular Networks for Perfusable Engineered 3D Tissues," *Nature Materials*, 11(9):768-774 (Jul. 1, 2012).

Kolesky, et al., "3D Bioprinting of Vascularized, Heterogeneous Cell-Laden Tissue Constructs," *Advanced Materials*, 26(19):3124-3130 (Feb. 18, 2014).

Zhao, et al., "The Integration of 3-D Cell-Printing and Mesoscopic Fluorescence Molecular Tomography of Vascular Constructs within Thick Hydrogel Scaffolds," *Biomaterials*, 33(21):5325-5332 (Apr. 22, 2012).

Examination Report No. 1 received in Australian Application No. 2014346959 dated Sep. 8, 2017 and reporting email dated Sep. 14, 2017.

Supplementary European Search Report and Written Opinion received in Application No. EP 14 85 9356 and reporting letter dated Sep. 7, 2017.

Ferris, C.J., et al., "Biofabrication: an overview of the approaches used for printing of living cells," *Appl Microbiol Biotechnol*, 97:4243-4258 (2013).

\* cited by examiner

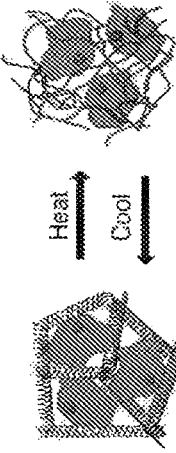
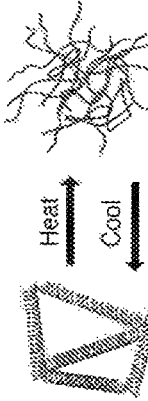
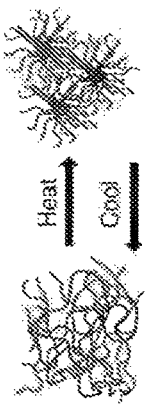
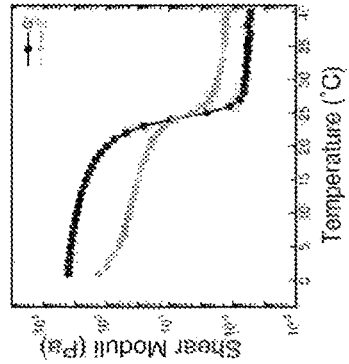
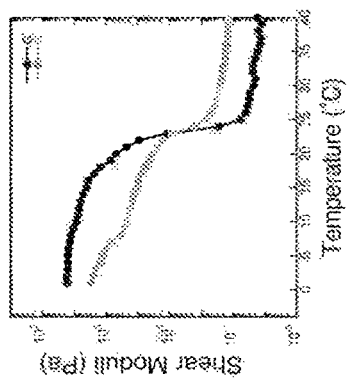
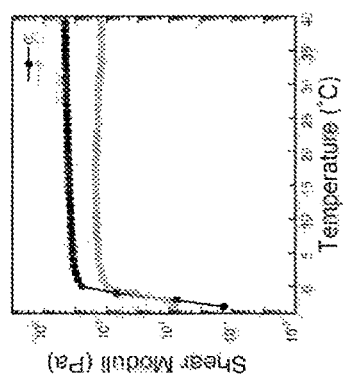
FIG. 6A FIG. 6C FIG. 6E
FIG. 6B FIG. 6D FIG. 6F

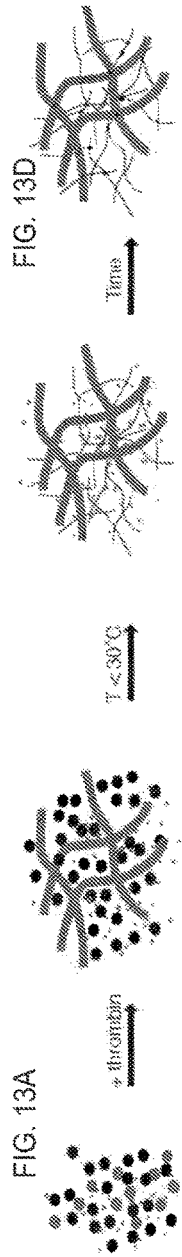

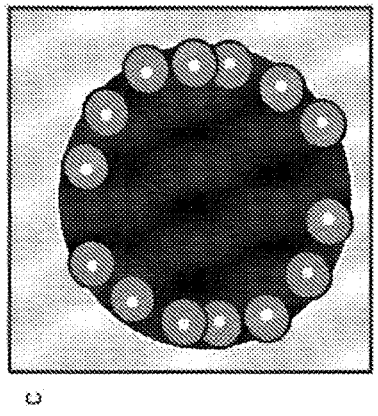
FIG. 16A
Print Endothelial cells
Endothelial cells dispersed in Pluronic F127 and 3D printed
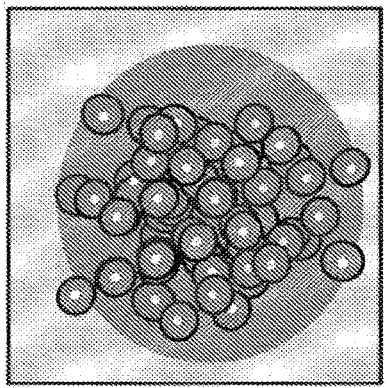
FIG. 16B
Matrix encapsulation
Channels are encapsulated with matrix material.
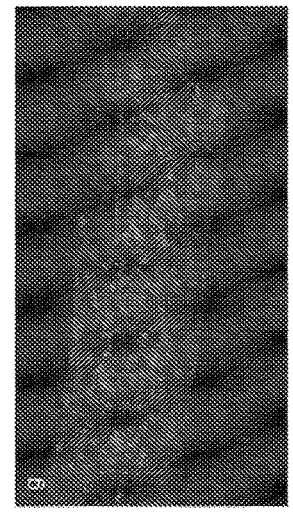
FIG. 16C
Evacuate
Structure is cooled to liquefy Pluronic F127. Left with a layer of cells on channel walls.
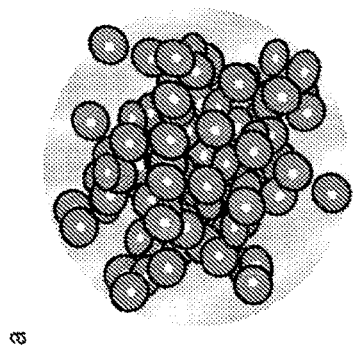
As printed
HUVEC-Pluronic
FIG. 16D
After casting and liquefying
FIG. 16E
After 1 day of incubation
FIG. 16F
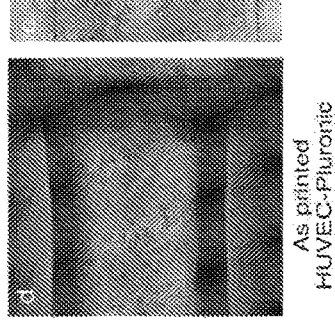
After active perfusion for 24hrs
FIG. 16G

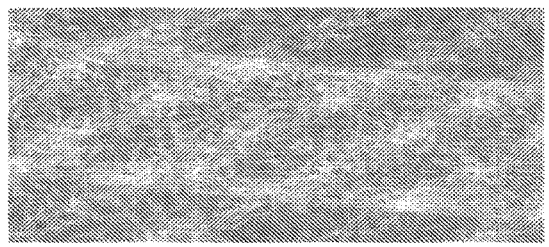
FIG. 17C
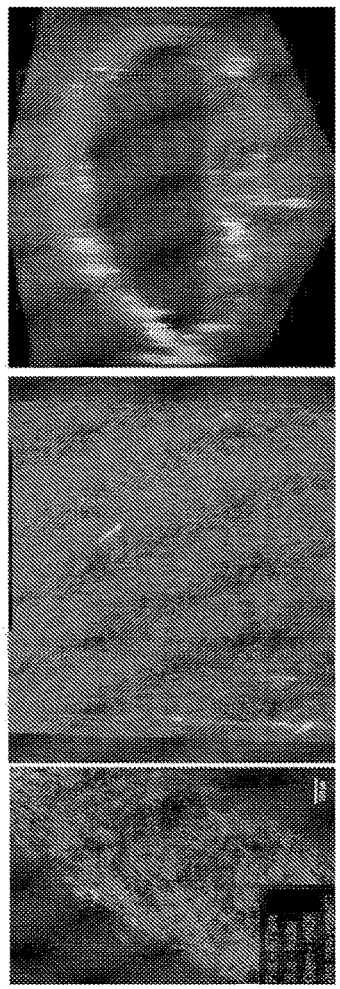
FIG. 17D
FIG. 17E
FIG. 17F

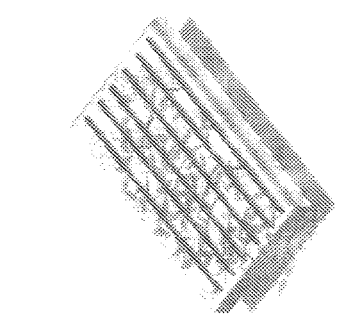
FIG. 19A
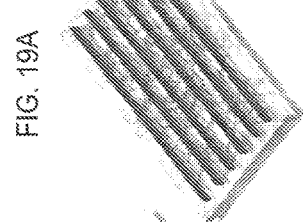
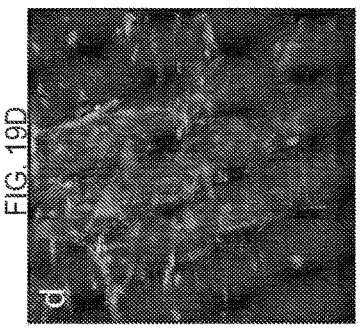
FIG. 19D
FIG. 19C
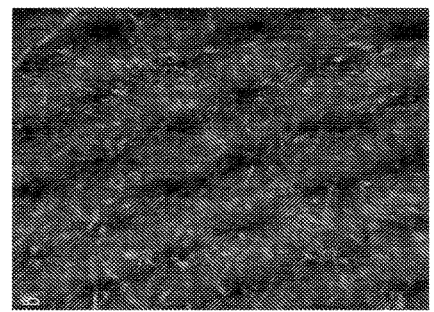
FIG. 19B
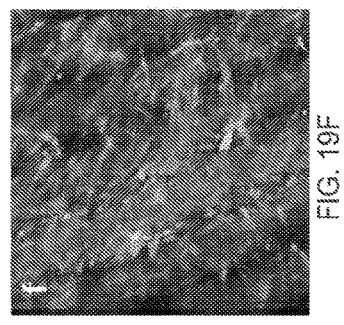
FIG. 19F
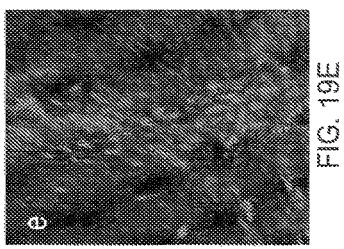
FIG. 19E

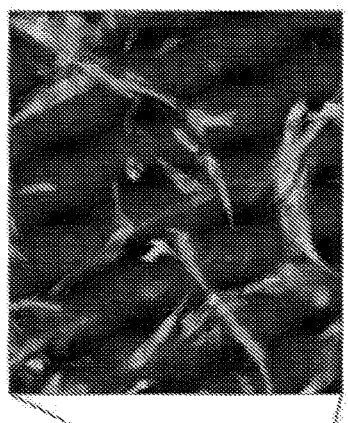
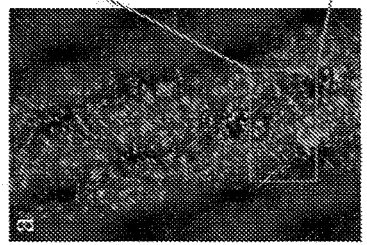
FIG. 20A
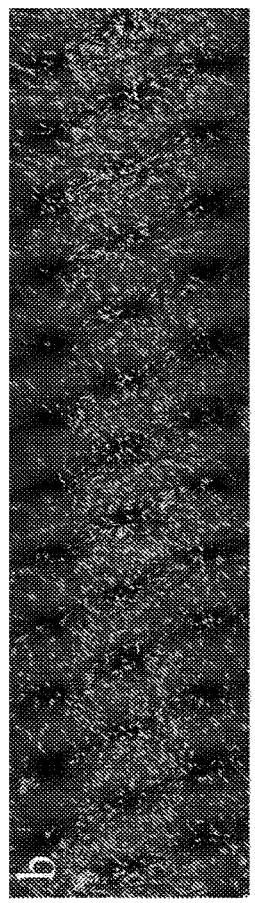
FIG. 20B
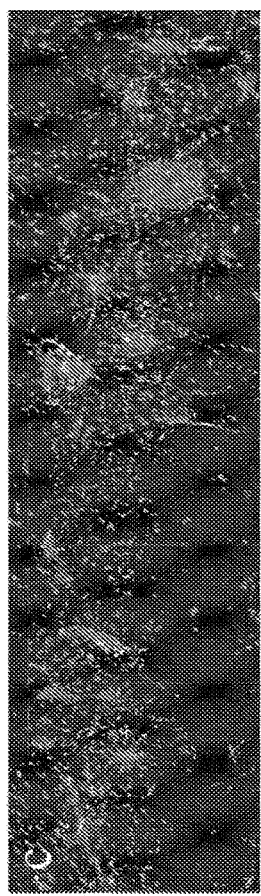
FIG. 20C

US 10,117,968 B2

METHOD OF PRINTING A TISSUE CONSTRUCT WITH EMBEDDED VASCULATURE

RELATED APPLICATIONS

The present patent document is a continuation application of the International Application Serial No. PCT/US2014/063810, filed Nov. 4, 2014, which claims the benefit of priority under 35 U.S.C. § 119 to U.S. Provisional Patent Application Ser. No. 61/900,029, filed on Nov. 5, 2013, which are hereby incorporated by reference in their entirety.

The following patents and patent application publications are also hereby incorporated by reference in their entirety: International Patent Application Serial No. PCT/US2012/044794, entitled "Multinozzle Deposition System for Direct Write Applications," filed Jun. 29, 2012; U.S. Patent Application Publication No. 2013/0084449, entitled "Viscoelastic Ink for Direct Writing of Hydrogel Structures," which was filed as PCT/US2011/29429 on Mar. 22, 2011; and U.S. Pat. No. 8,101,139, entitled "Microcapillary Networks," filed on Jun. 5, 2008.

FEDERALLY SPONSORED RESEARCH OR DEVELOPMENT

This invention was made with government support under contract number DMR 0820484 awarded by the National Science Foundation. The government has certain rights in the invention.

TECHNICAL FIELD

The present disclosure is related generally to tissue engineering and more particularly to fabricating tissue constructs including embedded vasculature.

BACKGROUND

The ability to create three-dimensional (3D) vascularized tissues on demand could enable scientific and technological advances in tissue engineering, drug screening, toxicology, 3D tissue culture, and organ repair. To produce 3D engineered tissue constructs that mimic natural tissues and, ultimately, organs, several key components—cells, extracellular matrix (ECM), and vasculature—may need to be assembled in complex arrangements. Each of these components plays a vital role: cells are the basic unit of all living systems, ECM provides structural support, and vascular networks provide efficient nutrient and waste transport, temperature regulation, delivery of factors, and long-range signaling routes. Without perfusable vasculature within a few hundred microns of each cell, three-dimensional tissues may quickly develop necrotic regions. The inability to embed vascular networks in tissue constructs has hindered progress on 3D tissue engineering for decades.

BRIEF SUMMARY

A printed tissue construct comprises one or more tissue patterns, where each tissue pattern comprises a plurality of viable cells of one or more predetermined cell types. A network of vascular channels interpenetrates the one or more tissue patterns. An extracellular matrix composition at least partially surrounds the one or more tissue patterns and the network of vascular channels.

A method of printing a tissue construct with embedded vasculature comprises depositing one or more cell-laden filaments, each comprising a plurality of viable cells, on a substrate to form one or more tissue patterns. Each of the one or more tissue patterns comprises one or more predetermined cell types. One or more sacrificial filaments, each comprising a fugitive ink, are deposited on the substrate to form a vascular pattern interpenetrating the one or more tissue patterns. The vascular pattern and the one or more tissue patterns are at least partially surrounded with an extracellular matrix composition. The fugitive ink is then removed to create vascular channels in the extracellular matrix composition, thereby forming an interpenetrating vascular network in a tissue construct.

A method of printing an epithelial tissue construct entails depositing one or more sacrificial filaments on a substrate to form a functional channel pattern. Each of the sacrificial filaments comprises a fugitive ink and a plurality of epithelial cells. The functional channel pattern is at least partly surrounded with an extracellular matrix composition. The fugitive ink is then removed to create one or more functional channels in the extracellular matrix composition. At least a portion of the epithelial cells remain in the one or more functional channels after removal of the fugitive ink, thereby forming an epithelial tissue construct.

A printed epithelial tissue construct comprises one or more functional channels comprising an epithelial layer thereon. An extracellular matrix composition at least partially surrounds the one or more functional channels.

BRIEF DESCRIPTION OF THE DRAWINGS

FIG. 6A shows a schematic of the sol-gel transition of Pluronic F127.

FIG. 6B shows the temperature dependence on the shear moduli (G' and G") of 40 wt. % Pluronic F127 ink.

FIG. 6O shows a schematic of the helix-to-coil transition characteristic of GelMA.

FIG. 6D shows the thermal dependence of GelMA shear moduli.

FIG. 6E shows GelMA laden with cells.

FIG. 6F shows the shear moduli as function of temperature for GelMA laden with 10T½ fibroblast cells.

FIGS. 13A-13D illustrate the synthesis of a fibrin-gelatin interpenetrating polymer network. First, gel precursors are mixed together with transglutaminase (TG). Then, by polymerizing fibrinogen via the enzyme thrombin, a fibrin network is formed. The second phase is then formed around the fibrin gel, and the two phases are slowly crosslinked together via TG.

FIGS. 13E-13F show mechanical properties of the fibrin-gelatin matrix material.

FIGS. 13G-13J show the diversity of the fibrin-gelatin matrix adhesivity for fibroblasts (connective tissue), smooth muscle cells, endothelial cells, and renal proximal tubule (epithelial) cells, respectively.

FIGS. 16A-16C show schematically the deposition of endothelial cells within a sacrificial filament formed from a fugitive ink, encapsulation of the sacrificial filament with an extracellular matrix composition, and evacuation of the fugitive ink to form a channel with endothelial cells lining the channel wall.

FIG. 16D shows an as-printed fugitive ink (Pluronic F127) comprising a dispersion of HUVECs; FIG. 16E shows the fugitive ink after casting and liquefying; FIG. 16F shows the vascular network after 1 day of incubation of the HUVECs; and FIG. 16G shows the vascular network after active perfusion for 24 hours.

FIGS. 17B-17C shows two functional channels in an extracellular matrix composition where the channels are lined with epithelial cells.

FIGS. 17D-17F show various confocal microscopy images of PTEC-lined channels and immunofluorescence images with various cell-specific proteins being expressed, including Na/K ATPase.

FIGS. 19A-19F show that, after printing a fugitive ink directly onto a cell-laden matrix, encapsulating with more cell-laden matrix, evacuating the fugitive ink to form vascular channels, and seeding the vascular channels with HUVECs, the endothelial cells form confluent layers and assemble into capillary structures over time.

FIGS. 20A-20C are confocal microscopy images that show spontaneous neovasculature formation in a printed cell-laden filament comprising two cell types (HNDFs and HUVECs dispersed within a gelatin-fibrin extracellular matrix material).

DETAILED DESCRIPTION

Figures 1A, 1B:
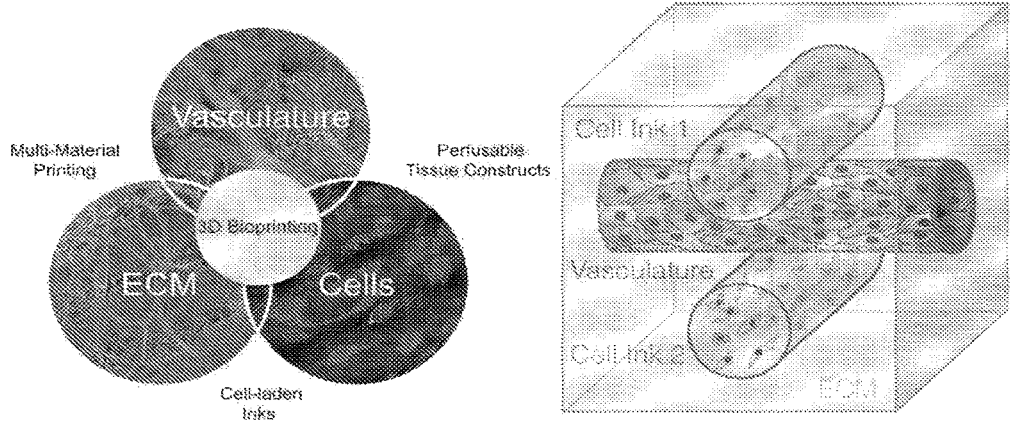
FIG. 1A shows an illustration of a bioprinting concept in which vasculature, an extracellular matrix, and cells may be printed in combination.
FIG. 1B shows a schematic of 3D printed heterogeneous tissue construct that includes vasculature and multiple cell types precisely placed in three dimensions.

A printed tissue construct including an interpenetrating vasculature and a method of printing such a tissue construct are described herein. FIG. 1A provides an illustration of the bioprinting concept. The printing method may enable the fabrication of heterogeneous 2D and 3D tissue constructs including cells, vasculature, epithelial ducts, and extracellular matrix in predetermined locations for applications ranging from 3D tissue culture and drug screen to organ transplants.

Figure 2A:
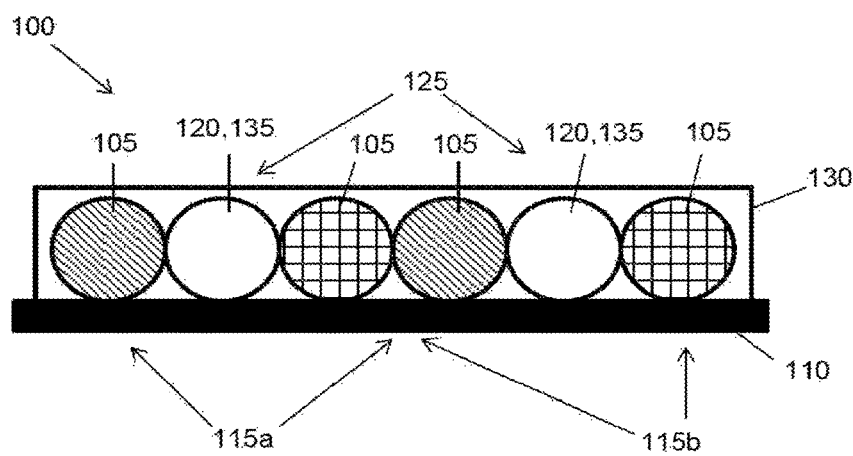
FIG. 2A is a cross-sectional schematic showing a 2D tissue construct including two tissue patterns and an interpenetrating vascular network.
Figure 2B:
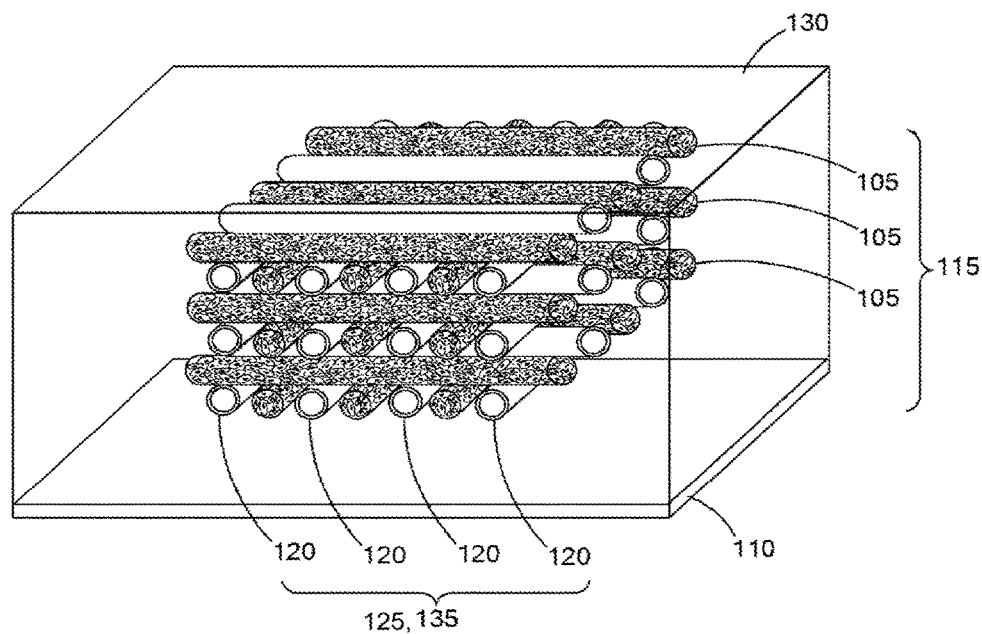
FIG. 2B shows an example of a 3D tissue construct including a tissue pattern and an interpenetrating vascular network.
Figure 2C:
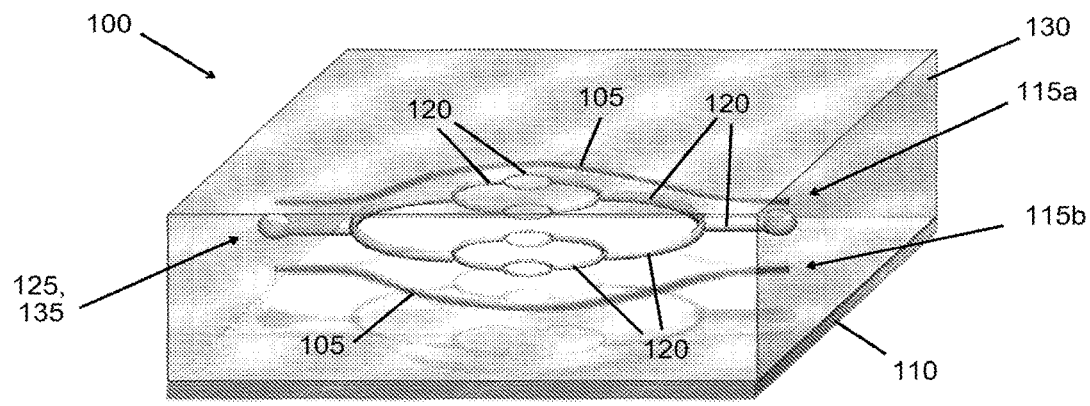
FIG. 2C shows an example of a 3D tissue construct including two tissue patterns and an interpenetrating vascular network.

FIG. 1B and FIGS. 2A-2C provide schematics showing exemplary printed tissue constructs that include vasculature and multiple cell types precisely placed in three dimensions. Referring to FIG. 2A or 2C, an exemplary printed tissue construct 100 comprises a first tissue pattern 115a and a second tissue pattern 115b, where each of the first and second tissue patterns 115a,115b comprises a plurality of viable cells of one or more predetermined cell types. For example, the first tissue pattern 115a may include cell types A and B, and the second tissue pattern 115b may include cell type C. An arrangement of one or more cell-laden filaments 105 comprising the viable cells and having the predetermined cell types may define each tissue pattern 115a,115b. In this example, the cell-laden filaments 105 that define the first tissue pattern 115a include cell types A and cell B, and the cell-laden filaments that define the second tissue pattern 115b include cell type C. A network of vascular channels 135 interpenetrates the tissue patterns 115a,115b. An extracellular matrix composition 130 at least partially surrounds the one or more tissue patterns 115a,115b and the network of vascular channels 135.

A pattern or network that "interpenetrates" another pattern or network in a printed tissue construct may be understood to comprise one or more filaments, channels or portions that are layered with, partially or completely overlapping, partially or completely underlapping, surrounding, embedded within, and/or interwoven with one or more filaments, channels or portions of the other pattern or network. A filament "deposited on a substrate" may be understood to be deposited directly on the substrate or directly on another filament, channel or portion previously deposited or formed on the substrate.

Referring now to FIG. 2B, a tissue construct comprising an embedded vasculature may be printed by depositing one or more cell-laden filaments 105, where each cell-laden filament 105 comprises a plurality of viable cells, on a substrate 110 to form one or more tissue patterns 115 (one tissue pattern in this example). The tissue pattern 115 comprises cells of one or more predetermined cell types. One or more sacrificial filaments 120, each comprising a fugitive ink, are also deposited on the substrate 110 to form a vascular pattern 125 that interpenetrates the one or more tissue patterns 115. The one or more tissue patterns 115 and the vascular pattern 125 are partially or fully surrounded by an extracellular matrix composition 130. The fugitive ink is then removed to create a network of vascular channels 135 in the extracellular matrix composition 130. Thus, an interpenetrating vascular network is formed in the tissue construct 100.

The tissue construct may include up to n different predetermined cell types. For example, n may satisfy $1 \leq n \leq 300$, $2 \leq n \leq 200$, or $2 \leq n \leq 100$. More typically, n is no more than 50, no more than 30, or no more than 20. For example, there may be 2 or more, 4 or more, 8 or more, 16 or more, or 20 or more predetermined cell types in the tissue construct.

As illustrated by the examples of FIGS. 2A-2C, each tissue pattern comprises or is defined by a two- or three-dimensional arrangement of one or more cell-laden filaments, and each tissue pattern (and thus each arrangement of cell-laden filaments) may comprise a different subset of the predetermined cell types. For example, in a tissue construct that includes 5 different predetermined cell types (e.g., cell types A, B, C, D, and E) and 3 different tissue patterns (e.g., tissue patterns 1, 2, and 3), tissue pattern 1, which is defined by a first arrangement of one or more cell-laden filaments, may comprise cell type A; tissue pattern 2, which is defined by a second arrangement of one or more cell-laden filaments, may comprise cell types B and C; and tissue pattern 3, which is defined by a third arrangement of one or more cell-laden filaments, may comprise cell types A and E.

In addition to the viable cells, the one or more cell-laden filaments may comprise a synthetic or naturally-derived biocompatible material that may be referred to as an extracellular matrix material. Each of the one or more cell-laden filaments may also or alternatively comprise one or more functional chemical substances (e.g., drugs, toxins, proteins and/or hormones) as described below. Each tissue pattern may include one layer or multiple layers of the cell-laden filament(s), which may in some embodiments be at least partially coalesced at regions of contact therebetween. For example, adjacent layers formed from one or more cell-laden filaments may be partially or fully coalesced depending on filament composition and the deposition (or post-deposition) conditions.

The arrangement of the cell-laden filaments in the tissue construct may be continuous or discontinuous. In a continuous arrangement, the cell-laden filaments of an exemplary tissue pattern (and comprising one or more predetermined cell types) may form a single interconnected tissue network in the tissue construct. For example, a single cell-laden filament comprising viable cells of the predetermined cell type(s) may be deposited in a single layer or in multiple layers to form the continuous arrangement. Alternatively, a plurality of cell-laden filaments comprising viable cells of the predetermined cell type(s) may be deposited in a single layer or in multiple layers to form the continuous arrangement, where each of the cell-laden filaments is in physical contact with, and possibly at least partially coalesced with, another cell-laden filament comprising the same predetermined cell type(s).

In a discontinuous arrangement of cell-laden filaments comprising one or more predetermined cell types, a single interconnected tissue network of the predetermined cell type(s) is not formed within the tissue construct. Instead, the cell-laden filaments comprising the predetermined cell type(s) may be dispersed uniformly or nonuniformly throughout the tissue construct. Consequently, the cells corresponding to the predetermined cell type(s) may also be dispersed uniformly or nonuniformly (e.g., in clumps) throughout the tissue construct. In this embodiment, some, all or none of the cell-laden filaments of a given tissue pattern and cell type(s) may be in physical contact with another cell-laden filament comprising cells of the same cell type(s).

Each of the one or more cell-laden filaments includes at least one viable cell and may include a large number of viable cells. For example, each of the cell-laden filaments may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration is no higher than about $10^9$ cells/ml, or no higher than about $10^8$ cells/ml. Consistent with this, the one or more tissue patterns of the tissue construct may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration in the tissue pattern is no higher than about $10^9$ cells/ml, or no higher than about $10^8$ cells/ml.

The cell concentration may be substantially uniform (e.g., within ±10%, within ±5%, or within ±1%) throughout each of the cell-laden filaments, and the cell concentration may also be substantially uniform throughout each of the tissue pattern(s). Alternatively, it is possible to deposit cell-laden filaments that include aggregates or clusters of cells that may range in size from about 10 cells/cluster to about 1000 cells/cluster, or from about 10 cells/cluster to about 100 cells/cluster. Such clusters may be dispersed uniformly or non-uniformly within the cell-laden filaments (and thus uniformly or non-uniformly throughout the one or more tissue patterns). Overall, the cell concentration may be substantially uniform throughout the tissue construct, or the cell concentration may include predetermined inhomogeneities within the tissue construct that may be defined by the location and morphology of the one or more tissue patterns, and/or by the cell distribution within the one or more tissue patterns.

The vascular network that interpenetrates the one or more tissue patterns is a two- or three-dimensional interconnected arrangement of vascular channels. The network may include one or more—furcations (e.g., bifurcations, trifurcations, etc.) from a parent vascular channel to a plurality of branching vascular channels. The network may have a hierarchical branching structure, where larger diameter channels branch into smaller diameter channels. Some or all of the vascular channels may follow a curved path, and thus may be considered to be curvilinear. All of the vascular channels in the network may have the same diameter, or at least one, some, or all of the vascular channels may have a different diameter. In some cases, one or more of the vascular channels may have a nonuniform diameter along a length thereof.

It is beneficial for the cells of the tissue construct to be close enough to the interpenetrating network of vascular channels to remain viable. One major problem with previous attempts to create tissue and organ-like structures is that necrotic regions could develop in areas without accessible perfusable vasculature. In the present work, each cell-laden filament, and thus each cell, may be placed in a location near to the vascular network, or near to where the vascular network may be formed. For example, at least a portion of the one or more cell-laden filaments forming each tissue pattern, and thus some or all of the viable cells, may be no more than about 1 mm away, no more than about 500 microns away, no more than about 300 microns away, no more than about 200 microns away, no more than about 100 microns away, no more than about 50 microns away, and/or no more than about 10 microns away from a vascular channel. One or more of the cell-laden filaments and thus at least some of the viable cells may be deposited so as to be in direct contact with a vascular channel. It is envisioned that some portion of the vascular network, for example the smallest capillaries, may be formed by angiogenesis and/or tubulogenesis after deposition of the sacrificial filaments and removal of the fugitive ink. For example, cell-laden filaments comprising endothelial cells may be deposited adjacent to the fugitive network to encourage tubulogenesis and/or angiogenesis to generate new capillaries.

Because the printing process described below for deposition of the cell-laden (and other) filaments allows for a high positional accuracy, the placement of the viable cells and/or the extracellular matrix material within the tissue construct may be controlled to within ±200 microns, within ±100 microns, within ±50 microns, within ±10 microns, or within ±1 micron.

Different types of cells may be placed in close proximity to one another by depositing a cell-laden filament that includes cells of more than one cell type, as discussed above. It is also contemplated that, in addition to the interpenetrating vasculature, one or more of the tissue patterns may interpenetrate one or more of the other tissue patterns so that certain types of cells may be positioned in close proximity to another. For example, one or more cell-laden filaments comprising a first type of cells (e.g., epithelial or endothelial cells) may be layered with, partially or completely overlapping, partially or completely underlapping, surrounding, embedded within, and/or interwoven with one or more cell-laden filaments comprising a second type of cells (e.g., smooth muscle cells). In some embodiments, all of the tissue patterns may interpenetrate at least one other tissue pattern, and it is also contemplated that all of the tissue patterns may interpenetrate all of the other tissue patterns.

The extracellular matrix composition may partially or fully surround the one or more tissue patterns, where a tissue pattern that is fully surrounded includes no exposed cell-laden filaments. The extracellular matrix composition may also partially or fully surround the network of vascular channels, where a vascular network that is fully surrounded includes no exposed vascular channels. For example, the network of vascular channels may be fully surrounded by the extracellular matrix composition, while the tissue pattern may be only partially surrounded by (e.g., adjacent to) the extracellular matrix composition. In such an example, the cell-laden filaments may be deposited after the vascular pattern is encapsulated. In some embodiments, the extracellular matrix composition may comprise additional viable cells and/or one or more functional chemical substances, as described below, which may be deposited along with the extracellular matrix composition. Such an extracellular matrix composition may be referred to as a cell-laden matrix. As described below, the extracellular matrix composition may be printed, cast or formed by another method known to one of ordinary skill in the art.

The tissue construct may have any desired 2D or 3D shape. For example, the tissue construct may have a planar geometry constructed from a single layer or multiple layers of cell-laden filaments and an interpenetrating vascular network. Such structures may have any desired height (thickness). Typically, the tissue construct has a height of about 100 cm or less, about 10 cm or less, about 1 cm or less, about 1 mm or less, about 500 microns or less, or about 100 microns or less, and typically at least about 10 microns, at least about 100 microns, at least about 200 microns, or at least about 1 mm, with applications ranging from tissue cultures and drug screening to skin constructs and corneal replacements.

Alternatively, the tissue construct into which a vascular network is embedded may have an arbitrary or application-dependent 3D size and shape. The tissue construct may have a solid structure, a porous structure, and/or a hollow structure (e.g., tubular or nontubular) and may be fabricated to mimic the morphology and function of particular organ. For example, the tissue construct may have the size and shape of a kidney, heart, pancreas, liver, bladder, vagina, urethra, trachea, esophagus, skin or other bodily organ. The 3D size and shape may in some cases be determined by a mold, as described below.

In general, in a three-dimensional arrangement of cell-laden filaments with an interpenetrating vascular pattern, the sacrificial filaments may have portions that overlie or underlie portions of the cell-laden filaments, and the sacrificial and cell-laden filaments may or may not be confined to an XY plane normal to the vertical direction (as defined by the force of gravity). The sacrificial filaments may be in physical contact with some or all of the cell-laden filaments, and, in some embodiments, the filaments may be partially or fully coalesced at the regions of contact. Both the sacrificial and cell-laden filaments may have spanning portions that extend unsupported between points of contact.

FIGS. 2A-2C show exemplary tissue constructs 100 each comprising one or more tissue patterns 115 interpenetrated by a vascular pattern 125 or a network of vascular channels 135. In FIG. 2A, two tissue patterns 115a,115b each comprising two cell-laden filaments 105 are deposited on the substrate 110 in a single layer. Adjacent to and/or in physical contact with the cell-laden filaments 105 are sacrificial filaments 120 of the vascular pattern 125, where each sacrificial filament 120 comprises a fugitive ink. After encapsulation with the extracellular matrix composition 130, the fugitive ink may be removed to form the network of vascular channels 135.

FIG. 2B shows a schematic of a tissue construct 100 comprising a 3D lattice structure 115 of cell-laden filaments 105 alternating with sacrificial filaments 120 of an interpenetrating vascular pattern 125. The fugitive ink making up the sacrificial filaments 120 is ultimately removed to create the network of vascular channels 135, which may also be visualized in FIG. 2B.

The tissue construct 100 of FIG. 2C includes two tissue patterns 115a,115b each defined by a curvilinear cell-laden filament 105 that are interpenetrated by a network of vascular channels 135 (or by a vascular pattern 125 comprising sacrificial filaments 120 if the fugitive ink has not yet been removed). The vascular network 135 has a hierarchical branching structure including curvilinear channels of various lengths and diameters. A solid substrate 110 is shown underlying the tissue construct 100; however, in this and in the other exemplary figures, the underlying solid substrate 110 may not be present.

Figure 3A:
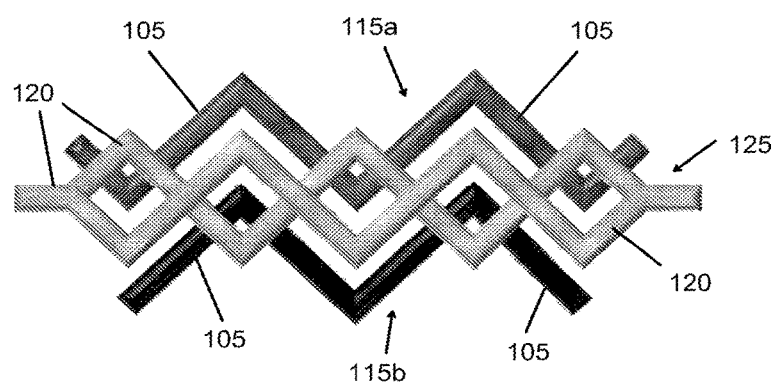
FIGS. 3A and 3B show examples of 3D tissue constructs including two tissue patterns and an interpenetrating vascular network.
Figure 3B:
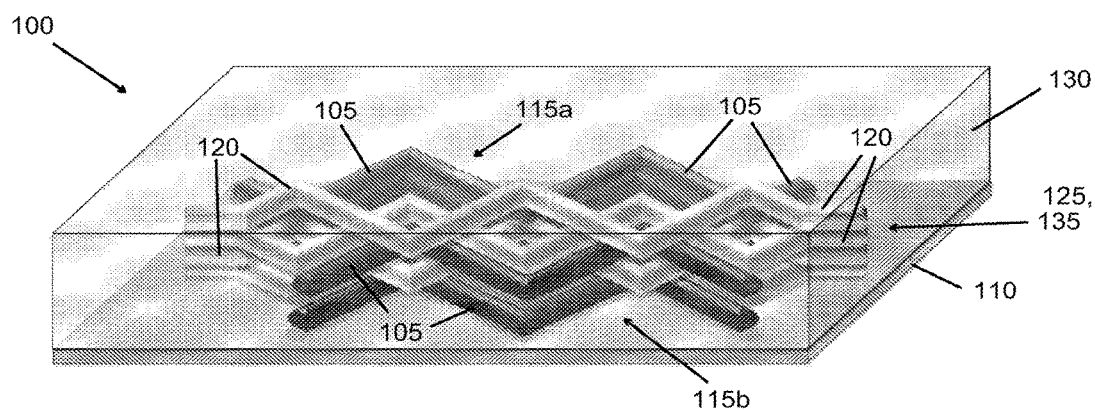

FIG. 3A shows a top view of two exemplary tissue patterns 115a,115b comprising cell-laden filaments 105 in a semi-woven configuration with sacrificial filaments 120 of a vascular pattern 125. FIG. 3B shows multiple layers of the same tissue patterns 115a,115b and vascular pattern 125 (or network of vascular channels 135 if the fugitive ink has been removed) surrounded by an extracellular matrix composition 130.

The viable cells and the predetermined cell types in the tissue construct may include any mammalian cell type selected from cells that make up the mammalian body, including germ cells, somatic cells, and stem cells. Depending on the type of cell, cells that make up the mammalian body can be derived from one of the three primary germ cell layers in the very early embryo: endoderm, ectoderm or mesoderm. The term "germ cells" refers to any line of cells that give rise to gametes (eggs and sperm). The term "somatic cells" refers to any biological cells forming the body of a multicellular organism; any cell other than a gamete, germ cell, gametocyte or undifferentiated stem cell. For example, in mammals, somatic cells make up all the internal organs, skin, bones, blood and connective tissue. As such, a cell may include any somatic cell isolated from mammalian tissue, including organs, skin, bones, blood and connective tissue (i.e., stromal cells). Examples of somatic cells include fibroblasts, chondrocytes, osteoblasts, tendon cells, mast cells, wandering cells, immune cells, pericytes, inflammatory cells, endothelial cells, myocytes (cardiac, skeletal and smooth muscle cells), adipocytes (i.e., lipocytes or fat cells), parenchyma cells (neurons and glial cells, nephron cells, hepatocytes, pancreatic cells, lung parenchyma cells) and non-parenchymal cells (e.g., sinusoidal hepatic endothelial cells, Kupffer cells and hepatic stellate cells). The term "stem cells" refers to cells that have the ability to divide for indefinite periods and to give rise to virtually all of the tissues of the mammalian body, including specialized cells. The stem cells include pluripotent cells, which upon undergoing further specialization become multipotent progenitor cells that can give rise to functional or somatic cells. Examples of stem and progenitor cells include hematopoietic stem cells (adult stem cells; i.e., hemocytoblasts) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; neural stem cells and neural progenitor cells that give rise to neuronal and glial cells; and muscle satellite cells (progenitor cells) that contribute to differentiated muscle tissue.

The tissue construct may also include one or more functional chemical substances selected from among drugs, toxins, proteins and/or hormones, including, but not limited to: growth factors, growth inhibitors, cytokines, steroids, and/or morphogens. Some cell specific examples include: bone morphogenic protein, vascular endothelial growth factor, fibroblast growth factors, including but not limited to VEGF, EGF, TGF-beta. The one or more functional chemical substances may be deposited with the cell-laden filament(s) and/or the sacrificial filaments and may diffuse into the surrounding extracellular matrix composition.

Figure 12A:
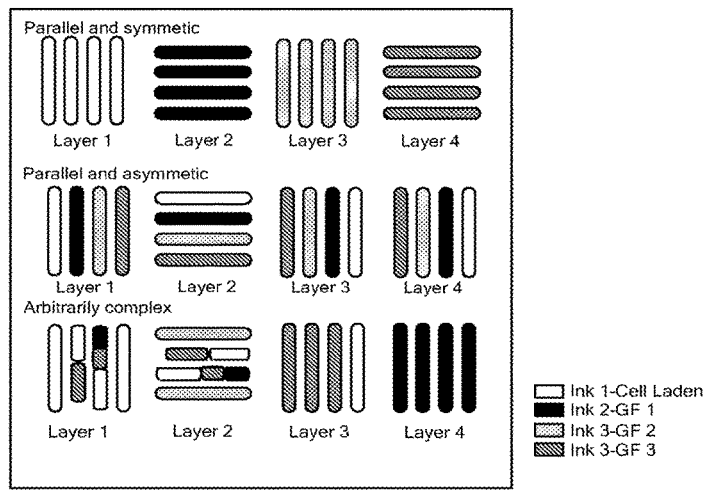
FIGS. 12A-12C show a schematic and images that illustrate the shaping of growth factor (GF) gradients by direct printing of a GF-laden extracellular matrix material comprising fibrin-gelatin.
Figure 12B:
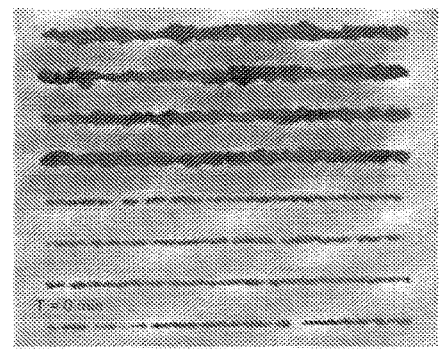
Figure 12C:
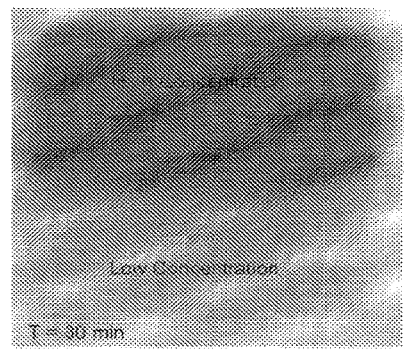
Figure 12D:
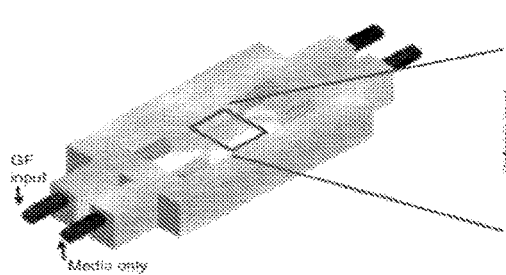
FIG. 12D show an exemplary mold for perfusion of parallel printed vascular channels with fluorescently labeled BSA in only one channel.
Figure 12E:
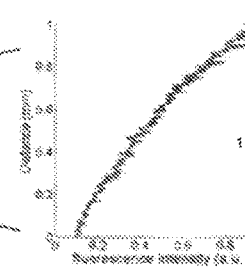
FIGS. 12E and 12F show that a nearly linear gradient is generated between the two channels of FIG. 12D in 24 hours.
Figure 12F:
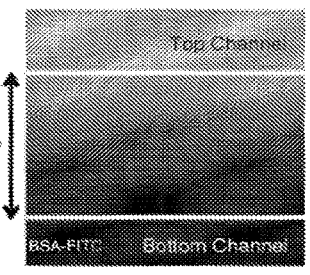

Such an approach may be used to generate gradients of cues within the extracellular matrix composition. Cells respond to gradients of fixed and diffusible chemical cues during development, wound healing and inflammatory responses that can direct cell migration, proliferation and differentiation. One method to introduce gradients of cues is to directly print cell-laden filaments preloaded with cues of interest, as illustrated in FIGS. 12A-12C, which may diffuse out upon encapsulation with an extracellular matrix composition to generate concentration gradients. Such gradients may or may not be anchored to the scaffold by action of transglutaminase. Alternatively, to generate fixed, long-term gradients, the channels formed by removing fugitive ink can be used to introduce factors that may diffuse into the surrounding extracellular matrix composition. For example, the formation of a linear gradient of fluorescently labeled BSA is demonstrated in FIGS. 12D-12F by creating a pair of parallel channels and flowing the fluorescent BSA through only one channel. At 24 hours, a near-linear gradient is apparent between the two channels (FIGS. 12E-12F).

The extracellular matrix material of the cell-laden filaments and the extracellular matrix composition that at least partially surrounds the tissue and vascular patterns may comprise a synthetic or naturally derived biocompatible material. The extracellular matrix material and the extracellular matrix composition may comprise the same or different biocompatible materials. Because the cell-laden filaments and, in some embodiments, the extracellular matrix composition may be deposited in a 3D printing process that entails extrusion through a micronozzle, as described below, it may be beneficial for one or both of the extracellular matrix material and the extracellular matrix composition to: (1) exhibit shear thinning behavior; (2) exhibit a defined yield stress $\tau_y$; and/or (3) have a shear elastic modulus G' and a shear viscous modulus G" modulus where G'>G" at room temperature.

In one example, the extracellular matrix material and/or the extracellular matrix composition may comprise a gel. An ideal gel for bioprinting applications may exhibit a rapid transition from a low viscosity solution to a solid-like gel, which may be seen by an initial increase in shear elastic modulus. Rapid, controllable gelation may enhance printed structure fidelity by minimizing or obviating swelling and dissociation typical of slow gelation processes. The term "gel" may refer to a semi-solid substance that may comprise a gelling agent to provide viscosity or stiffness. The gel may be formed upon use of a gelling agent, such as a thickening agent, crosslinking agent or a polymerization agent, and may comprise a cross-linked structure or a non-cross-linked structure. The gel may be hydrophobic or hydrophilic. Some examples of suitable gels include a hydrogel, thermo-reversible gel, a photo-sensitive gel, a pH sensitive gel, a peptide gel, or a cell type specific gel. Additional examples of gels include silica gel, silicone gel, aloe vera gel, agarose gel, nafion, polyurethane, elastomers (thermoplastic, mineral-oil thermoplastic, etc.), ion-exchange beads, organogels, xerogels and hydrocolloids. Hydrogels include those derived from collagen, hyaluronate, fibrin, alginate, agarose, chitosan, gelatin, matrigel, glycosaminoglycans, and combinations thereof. In one example, the gel may comprise gelatin methacrylate (GelMA), which is denatured collagen that is modified with photopolymerizable methacrylate (MA) groups. Suitable hydrogels may comprise a synthetic polymer. In certain embodiments, hydrogels may include those derived from poly(acrylic acid) and derivatives thereof, poly(ethylene oxide) and copolymers thereof, poly(vinyl alcohol), polyphosphazene, and combinations thereof. The extracellular matrix material and/or the extracellular matrix composition may comprise a naturally derived biocompatible material, such as one or more extracellular matrix components, including collagen, fibronectin, laminin, hyaluronates, elastin, and/or proteoglycans. Other suitable biocompatible materials for the extracellular matrix material and/or the extracellular matrix composition may include variations of cellulose, Matrigel, acrylates, acrylamides, polylactic co-glycolic acid, epoxies, aldehydes, ureas, alcohols, polyesters, silk, proteins, glycosaminoglycans, carbohydrates, minerals, salts, clays, hydroxyapatite, and/or calcium phosphate.

In a preferred embodiment, the extracellular matrix material and/or the extracellular matrix composition may comprise gelatin and fibrin. The gelatin and fibrin may form an interpenetrating polymer network that mimics natural extracellular matrix (ECM) and may be optimized for cell attachment, bioprinting, transparency, and biocompatibility. The fibrin-gelatin interpenetrating polymer network may be created by mixing solutions of fibrinogen and gelatin with transglutaminase (TG), a slow-acting $Ca^{2+}$ dependent enzyme, to create a gel-precursor solution that may later be mixed with bovine thrombin to create a fibrin gel backbone, as illustrated in FIGS. 13A-13D. Fibrin may be made from a concentrated fibrinogen solution that has been activated by bovine thrombin and calcium chloride. Fibrin is a rapidly coagulating phase that permits rapid, controllable gelation of a printed structure. Advantageously, fibrin and gelatin can be welded together via mobile surface chain entanglement, while forming a strong interface. Creating monolithic gels of this nature is possible due to the slow crosslinking kinetics of transglutaminase (TG). Although thrombin rapidly induces fibrin gel formation, the gelatin present in the IPN allows one to print sacrificial ink on the already cast layer, and, ultimately, to encapsulate with liquid gelatin-fibrin. The two phases may weld together, creating a monolithic gel. This material system, which is discussed further below in the Examples, can be readily tailored to modify gelation kinetics, interface adhesion, mechanical properties, optical properties, and cell-material interactions.

As described above, one or more sacrificial filaments comprising a fugitive ink may be deposited on a substrate to form a vascular pattern that interpenetrates one or more tissue patterns. The vascular pattern comprises a two- or three-dimensional interconnected arrangement or network of the one or more sacrificial filaments. Removal of the fugitive ink after partial or complete encapsulation with the extracellular matrix composition creates a perfusable network of vascular channels in the tissue construct. Because, like the cell-laden filaments, the sacrificial filaments may be deposited in a 3D printing process that involves extrusion through a micronozzle, it may be advantageous for the fugitive ink to: (1) exhibit shear thinning behavior; (2) exhibit a defined yield stress $\tau_y$; and/or (3) have a shear elastic modulus G' and a shear viscous modulus G" modulus where G'>G" at room temperature.

Figure 21A:
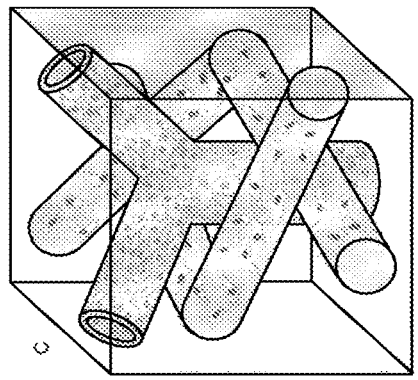
FIG. 21A shows a schematic depicting an embedded printing process.
Figure 21B:
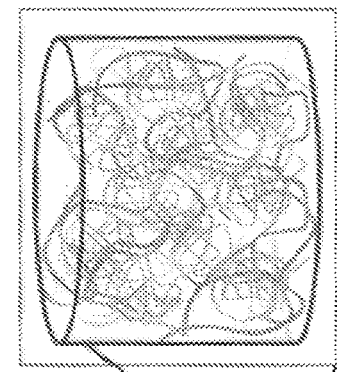
FIG. 21B shows a schematic of an extracellular matrix composition comprising a semi-interpenetrating polymer network (IPN) (e.g., PAA-GelMA) suitable for embedded printing.
Figure 21C:
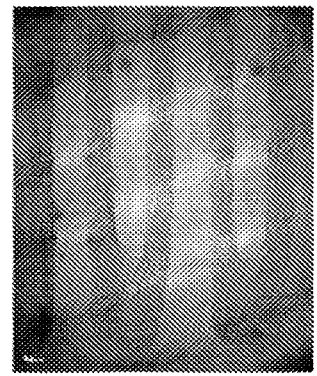
FIG. 21C illustrates a complex heterogeneous structures with arbitrary 3D shape that may be constructed by embedded printing.

The substrate for deposition typically comprises a material such as glass or other ceramics, PDMS, acrylic, polyurethane, polystyrene or other polymers. In some embodiments, the substrate may comprise living tissue or dehydrated tissue, or one of the extracellular matrix compositions described above. The substrate may be cleaned and surface treated prior to printing. For example, glass substrates may undergo a silane treatment to promote bonding of the cell-laden filaments to the glass substrate. In some embodiments, it is envisioned that the substrate may not be a solid-phase material but may instead be in the liquid or gel phase and may have carefully controlled rheological properties, as described, for example, in W. Wu et al., Adv. Mater. 23 (2011) H178-H183, which is hereby incorporated by reference. In the work of Wu et al., a fugitive ink was printed directly into synthetic hydrogels to create network structures. However, these synthetic materials do not support cell attachment and proliferation, limiting their use to non-biological applications. In the present disclosure, an extracellular matrix composition that facilitates cell attachment, migration, proliferation, and tissue-specific function while maintaining the appropriate rheology for printing is described. The cell-laden and sacrificial filaments are embedded in the extracellular matrix composition during printing, and thus the at least partial surrounding of the tissue and vascular patterns with the extracellular matrix composition occurs during deposition of each of the cell-laden and sacrificial filaments, as shown schematically in FIG. 21A. This includes arbitrarily complex 3D structures that may require support material during printing, as shown for example in FIG. 21C. When the forming and embedding of the tissue and vascular patterns occurs simultaneously, as described above, the substrate onto which deposition occurs may be considered to be the container that holds the extracellular matrix composition or the extracellular matrix composition itself.

To form the extracellular matrix composition, a microgel (e.g., a poly(acrylic acid) (PAA) microgel) may be used as a rheological modifier and blended with one or more extracellular matrix materials, as set forth previously, such as gelatin methacrylate. A semi-interpenetrating polymer network (semi-IPN) may be formed, as shown schematically in FIG. 21B. Microgels may be understood to comprise colloidal gel particles that are composed of chemically cross-linked three-dimensional polymer networks. Microgels may act as sterically stabilized colloids with only a shell and no core. They can vary in composition and may include PAA, polystyrenes, PEG, and/or other biomaterials. It is contemplated that a natural extracellular matrix or biomaterial may be converted into a microgel form to impart the ideal rheology. Examples of suitable biomaterials include hyaluron, collagen, alginate, fibrin, albumin, fibronectin, elastin, or matrigel. Alternatively, synthetic materials such as PEG, acrylates, urethanes, or silicones may be modified in a similar manner.

Figure 21D:
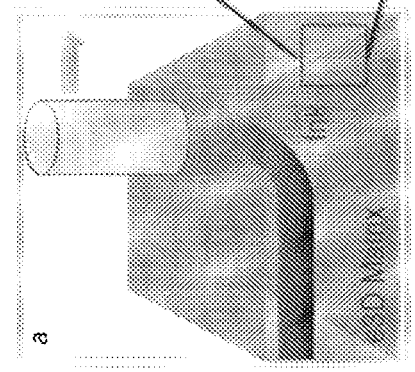
FIG. 21D provides representative rheological measurements of ink and matrix rheology appropriate for embedded printing.
Figure 21E:
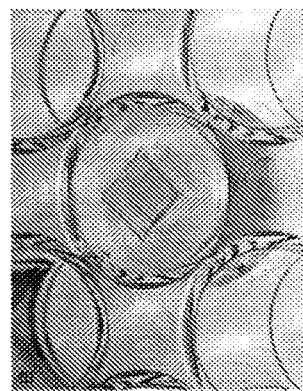
FIG. 21E is a photograph of a vascular cube including a vascular network formed by embedded printing.
Figure 21F:
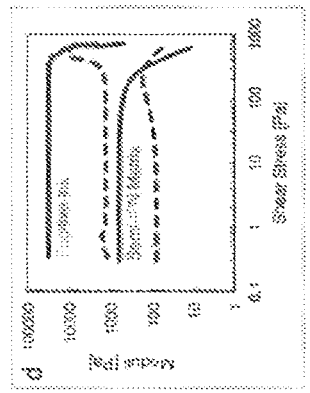
FIG. 21F shows a printed cell-laden filament within a semi-IPN extracellular matrix composition.
Figure 22:
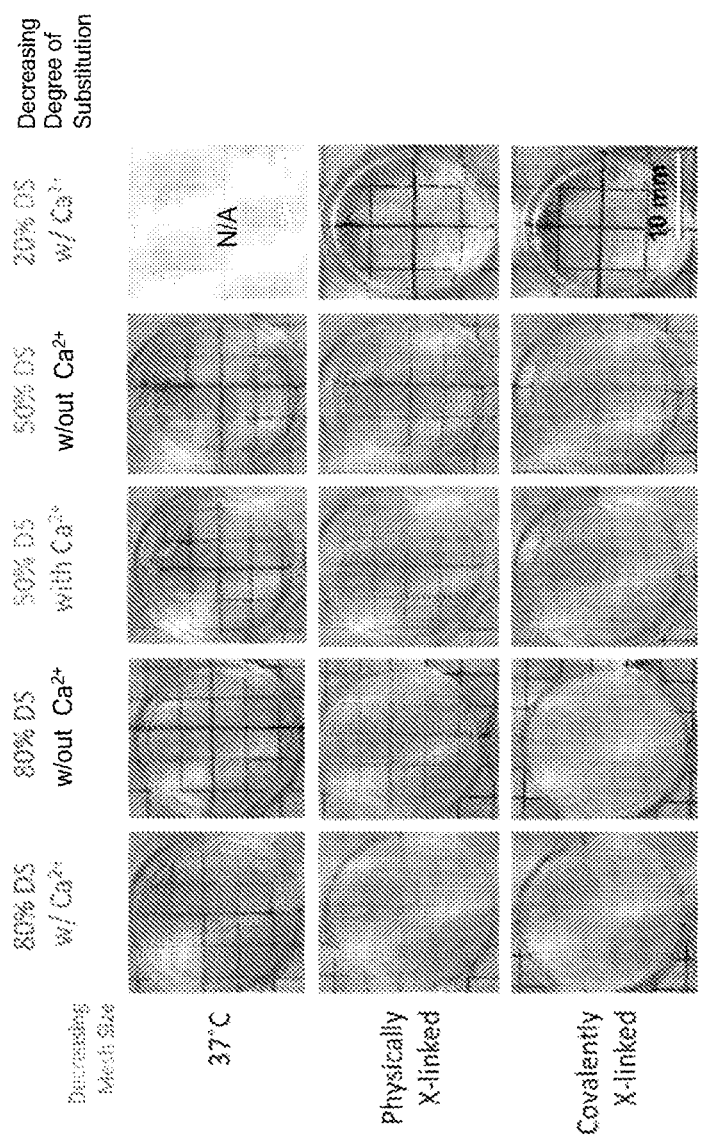
FIG. 22 demonstrates that the transparency of a semi-IPN extracellular matrix composition may be tuned by degree of substitution (DS).

Representative rheological measurements of ink and matrix rheology that are appropriate for embedded printing are shown in FIG. 21D. In one example, a high molecular weight (>1.25 MDa) PAA microgel is used as a rheological modifier and blended with gelatin-methacrylate (GelMa) to create an extracellular matrix composition that supports the creation of complex 3D vascular networks, which can be endothelialized as described previously. The transparency of the extracellular matrix composition may be altered by varying the degree of substitution and mesh size, as shown in FIG. 22. FIG. 21E shows a vascular cube demonstrating the control over the embedded printing of 3D vascular networks, and FIG. 21F shows a printed cell-laden filament within a PAA-GelMA extracellular matrix composition.

The method may further include, prior to surrounding or encapsulating the tissue and vascular patterns with the extracellular matrix composition, depositing one or more structural filaments layer by layer on the substrate in a predetermined pattern to form a mold. The structural filaments may comprise one or more structural materials selected from among the exemplary extracellular matrix compositions or extracellular matrix materials provided above. The mold may hold the extracellular matrix composition during the encapsulation and may remain as part of the tissue construct, or it may be removed after processing. The structural filaments may define the perimeter of the tissue construct on the substrate and all or at least a portion of the three-dimensional shape of the tissue construct out of the XY plane.

The mold may also have other functionalities besides defining the shape of the tissue construct. For example, the mold may serve as an interface for perfusion of channels in a printed tissue construct. FIGS. 15A-15D and 15E-15G show exemplary designs of printed molds or interface structures. The exemplary mold shown in FIGS. 15A-15D is designed for passive rocking perfusion. The mold, which may also be referred to as an interface structure, can hold vascularized tissue in place during rocking by immobilizing the tissue construct between a base portion of the mold, which may comprise PDMS, and an overlying cover, which may comprise glass.

Figure 15A:
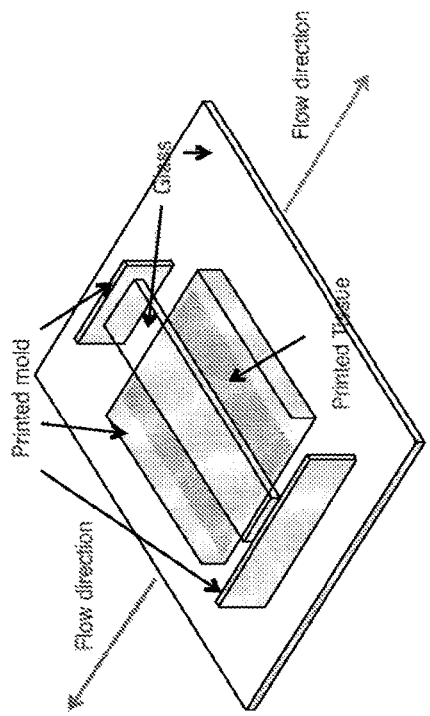
FIGS. 15A-15D show an exemplary mold for passive rocking perfusion of a tissue construct.
Figure 15B:
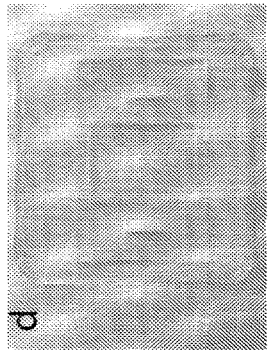
Figure 15C:
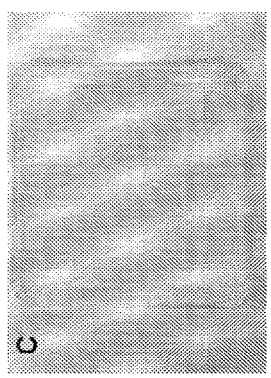
Figure 15D:
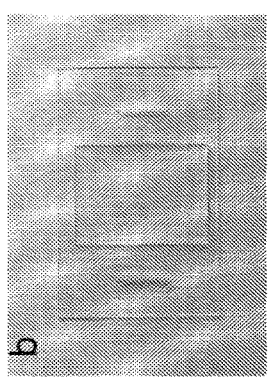
Figure 15F:
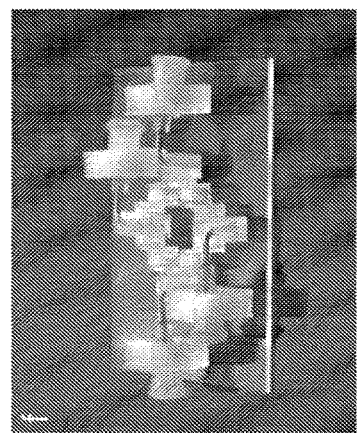
FIGS. 15E-15G show exemplary molds for active pump-based perfusion of a tissue construct.
Figure 15G:
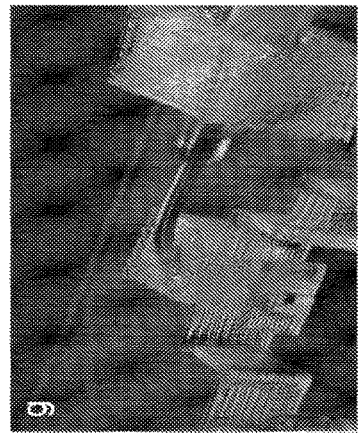
Figure 15E:
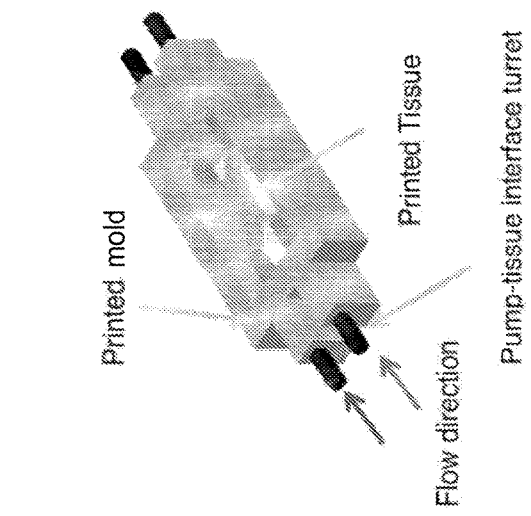

The mold designs of FIGS. 15E-15G enable active pump-based perfusion of a tissue construct and include flow channels that are in fluid communication with (e.g., contiguous with) the vascular channels of the tissue construct. Conduits that serve as flow channels may be partially or fully embedded in the mold itself and hollow pins (e.g., metal pins) may be used to interface with the vascular channels, as shown in FIGS. 15F-15G. The exemplary mold shown in FIG. 15E has a wall with multiple buttresses that contain the flow channels, which include hollow pins extending into the interior of the mold, where the tissue construct is fabricated. The vascular channels of the tissue construct may be contiguous with apertures of the hollow pins to enable flow to be introduced into the vascular channels from tubing connected to the flow channels, and fluid may be removed from the vascular channels through one or more other apertures.

In one example, the mold may be formed of an elastomeric silicone, a structural material known to be viscoelastic, non-toxic, biocompatible, and capable of forming reversible press-to-fit seals. The structural material may be 3D printed to form one or more uncured structural filaments comprising one or more of silicone, epoxies, esters of acrylic acid, or one of the extracellular matrix compositions provided above. After printing is complete, the structural filament(s) may be cured (e.g. by heating or photopolymerizing) for a suitable time duration (e.g., about one hour or more), after which the mold may exhibit the desired material properties.

The encapsulation of the tissue and vascular patterns may comprise casting a liquified matrix precursor into the mold and gelling the matrix precursor to form the extracellular matrix composition. Casting of the matrix precursor may take place at a temperature of from about 25° C. to about 40° C. For example, gelatin methacrylate, or GelMA, may be cast at a temperature of about 37° C. After casting, the matrix precursor may be cooled (e.g., to about 15° C. in the case of GelMA) to form a rigid physical gel. Alternatively, the encapsulation may occur during deposition of the tissue and vascular patterns in an embedded or omni-directional 3D printing process, as indicated above. It is also contemplated that the extracellular matrix composition may be deposited by filament deposition, similar to the cell-laden and sacrificial filaments. For example, one or more ECM filaments comprising the extracellular matrix composition may be extruded from a nozzle and deposited on the substrate layer by layer to build up the desired 3D geometry, as described below. In such a case, it may not be necessary to employ a mold to contain the extracellular matrix composition.

The extracellular matrix composition may be cured before or after removal of the fugitive ink to form a permanently chemically cross-linked structure. Depending on the extracellular matrix composition, the curing may entail heating, UV radiation or chemical additives (e.g., enzymatic curing).

Any or all of the filaments deposited on the substrate—including the cell-laden filaments defining the one or more tissue patterns, the one or more sacrificial filaments defining the interpenetrating vascular pattern or a functional channel pattern, the one or more structural filaments that may define the mold, and/or the one or more ECM filaments that may yield the extracellular matrix composition—may be extruded from a nozzle before being deposited on the substrate. In the discussion of the extrusion process that follows, the sacrificial filaments, the cell-laden filaments, the structural filaments and/or the ECM filaments may be collectively referred to as "the filaments" since the processing steps may be applicable to any or all of the filament compositions.

Figure 4:
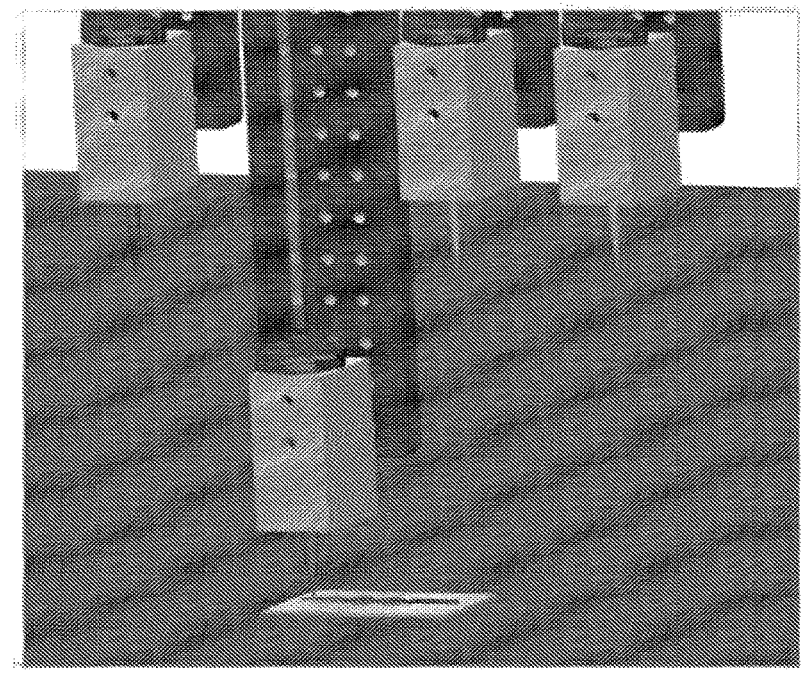
FIG. 4 shows four print heads (nozzles) mounted onto a custom 3D printer where each z-axis is controlled independently.
Figures 5A, 5B, 5C:
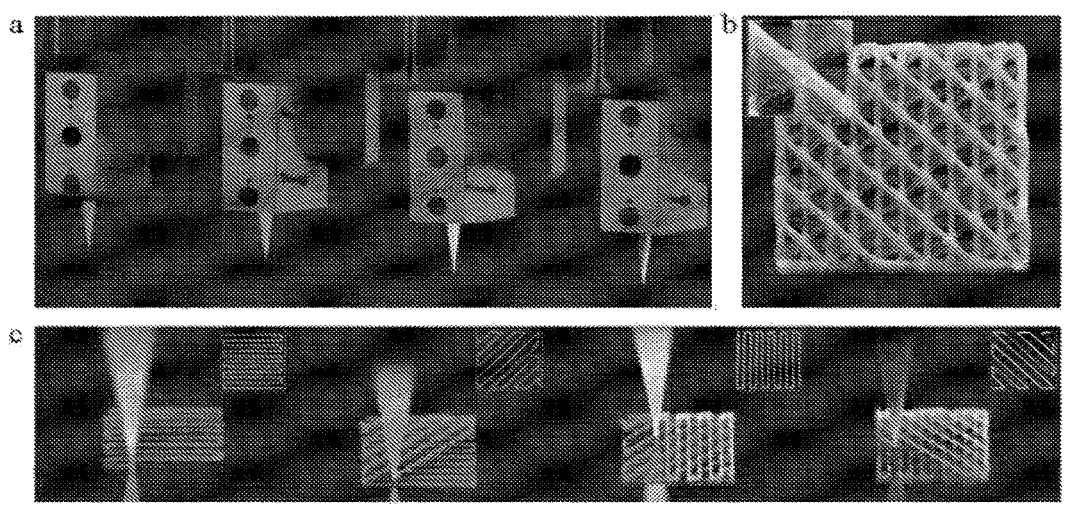
FIG. 5A also shows four print heads (nozzles)
FIG. 5B shows a four-layer microstructure where complex ink patterns are deposited sequentially from four nozzles to form the four-layer microstructure with varied composition.
FIG. 5C shows sequential fabrication images of each layer of the deposition process, where each inset illustrates the geometry of each layer.

FIG. 4 shows four exemplary nozzles or print heads that may be employed to extrude the filaments and deposit them on the substrate. The nozzles shown are part of a custom-built 3D printer comprising a large build platform (750 mm×650 mm) equipped with four independent z-axes. FIGS. 5A-5C provide a demonstration of the 3D printing of a four-layer, multimaterial construct by sequential deposition of a filament of a different composition from each of the four nozzles. The insets of FIG. 5C show, for each layer, the repeating unit of the 3D structure.

Although there are four nozzles for the exemplary printer of FIGS. 4 and 5A, the number of nozzles employed to form the tissue construct by 3D printing may be lower or higher. In general, 1 or more, 2 or more, 3 or more, 4 or more, 5 or more and up to N nozzles may be used for extruding the filaments, where $1 \leq N \leq 1024$, and more typically N is no more than 512, N is no more than 256, N is no more than 128, or N is no more than 64. The filaments may be extruded from the N nozzles sequentially in a serial deposition process or simultaneously in a parallel deposition process, where each nozzle may contain a different precursor ink (e.g., a cell-laden ink comprising one or more predetermined cell types, a fugitive ink, a structural ink, or an ECM ink). It is also contemplated that the deposition may include both parallel and serial deposition steps. To facilitate sequential or serial printing, the nozzles can be independently controlled in the z-direction, as shown in FIG. 4.

Each nozzle may have an inner diameter of from about 1 micron to about 1 mm in size, and more typically from about 50 microns to about 500 microns. The size of the nozzle may be selected depending on the desired filament diameter. Depending on the injection pressure and the nozzle translation speed, the deposited filament may have a diameter ranging from about 1 micron to about 10 mm, and more typically from about 100 microns (0.1 mm) to about 1 mm. The inks fed to the nozzles may be housed in separate syringe barrels that may be individually connected to a nozzle for printing by way of a Luer-Lok™ or other connector. The extrusion of each of the filaments may take place under an applied pressure of from about 1 psi to about 200 psi, from about 10 psi to about 80 psi, or from about 20 psi to about 60 psi. The pressure during extrusion may be constant or it may be varied. By using alternative pressure sources, pressures of higher than 100 psi or 200 psi and/or less than 1 psi may be applied during printing. A variable pressure may yield a filament having a diameter that varies along the length of the filament. Such an approach may be used, for example, to form the branching, hierarchical vascular network shown in FIG. 2C and in FIGS. 7E-7F, which is formed from sacrificial filaments of various lengths and diameters. The extrusion may be carried out at ambient or room temperature conditions (e.g., from about 18° C. to about 25° C.).

During the extrusion and deposition of each filament, the nozzle may be moved along a predetermined path (e.g., from $(x_1, y_1, z_1)$ to $(x_2, y_2, z_2)$) with a positional accuracy of within ±100 microns, within ±50 microns, within ±10 microns, or within ±1 micron. Accordingly, the filaments may be deposited with a positional accuracy of within ±200 microns, within ±100 microns, within ±50 microns, within ±10 microns, or within ±1 micron. The nozzles may be moved and the filaments may be deposited at speeds as high as about 3 m/s (e.g., from about 1 cm/s to about 3 m/s), and are more typically in the range of from about 1 mm/s to about 500 mm/s, from about 1 mm/s to about 100 mm/s, or from about 1 mm/s to about 10 mm/s.

The predetermined path of the nozzle may have an XY boundary area of at least about 2400 cm$^2$, at least about 2700 cm$^2$ and up to about 1 m$^2$ as determined by the size of the build platform of the printer. For example, the build platform may have a length of from about 60 cm to about 100 cm and a width of from about 40 cm to about 100 cm. Each print head may be moved in the z-direction a distance from about 10 cm to about 50 cm, or about 15 to about 30 cm.

The deposited filaments are formed from precursor inks (e.g., cell-laden inks comprising one or more predetermined cell types, fugitive inks, structural inks, or ECM inks) having a suitable composition and rheological properties. The precursor inks may be viscoelastic and comprise a viscosity with a non-linear shear dependence. The viscosity of the precursor inks may fall in the range of from about 0.001 Pa-sec to about 10,000 Pa-sec. The precursor inks may optionally include viscosifiers to help control the rheological properties. Each cell-laden ink, and optionally, the fugitive and/or ECM ink, may include one or more cells of one or more predetermined cell types in a carrier that may be a liquid or a gel. The carrier may include, in addition to an extracellular matrix material as described above, one or more functional chemical substances as described above. The carrier may also or alternatively include a cell culture medium designed to support the growth of cells. In one example, to form a cell-laden ink comprising viable cells mixed with a hydrogel, a predetermined amount of a hydrogel precursor powder is mixed with a cell culture medium to form a solution of an appropriate composition. The cells of interest are then dispersed in the solution at the desired cell concentration (e.g., any of the cell concentrations set forth above for the cell-laden filaments), and mixed thoroughly. Steps to prepare exemplary cell-laden GelMA inks, cell-laden gelatin-fibrin inks, Pluronic F127 fugitive inks, and PDMS structural inks are described in the Examples below.

After encapsulation of the tissue and vascular patterns, the fugitive ink may be removed to form a network of vascular channels in the extracellular matrix composition. The fugitive ink may comprise a biocompatible material and may be designed for compatibility with the cell-laden formulations and the extracellular matrix composition during room temperature deposition. Suitable fugitive inks may include, for example, Pluronic F127, Pluronic F123, agarose, sugar, wax, and fatty oils (e.g., animal fat derived oils such as Crisco). If a hydrogel is employed for the extracellular matrix composition (and/or the extracellular matrix material), and a hydrogel such as Pluronic F127 is employed as the fugitive ink, it may be advantageous for the fugitive ink and the matrix hydrogel to have similar water contents (e.g., within ±30%) to avoid distortion of the fugitive ink after printing. The fugitive ink and the extracellular matrix composition may also be selected to have complementary thermal transitions, as discussed further below.

Pluronic F127 is an FDA-approved material that is biologically inert to multiple cell types over the short time periods needed to complete the fabrication process. The material includes a hydrophobic poly(propylene oxide) (PPO) segment and two hydrophilic poly(ethylene oxide) (PEO) segments arranged in a PEO-PPO-PEO configuration. Pluronic F127 undergoes thermally reversible gelation above a critical micelle concentration (CMC; about 21 wt. %) and the gelation temperature. The gelation temperature decreases from approximately 10° C. to 4° C. as the PEO-PPO-PEO concentration increases. When both of these critical parameters are exceeded, micelles form as the hydrophilic PEO segments self-assemble into corona that are well solvated by water, while the hydrophobic PPO segments tightly associate within the micelle cores. However, below the gelation temperature, the hydrophobic PPO units are hydrated, such that individual PEO-PPO-PEO species become soluble in water giving rise to a gel-to-fluid transition for systems whose concentration exceeds the CMC. Thus, the material liquifies upon cooling below the gel point.

It is important that the patterned cells and surrounding extracellular matrix composition are not damaged during deposition of the sacrificial filaments or removal of the fugitive ink, and thus it is preferred that harsh solvents and/or elevated temperatures are not utilized during the removal process. With proper selection of the fugitive ink and the extracellular matrix composition/material, the fugitive ink may be removed without damage to the tissue construct. For example, if the fugitive ink undergoes a gel-to-fluid transition as described above, cooling of the vascular pattern after encapsulation may be effective for removal of the fugitive ink. To remove Pluronic F127, the vascular pattern may be cooled to a temperature of no more than about 1° C., depending on the concentration. It is also contemplated that the fugitive ink may be dissolved in a suitable aqueous solution for removal. Once the fugitive ink is liquefied or dissolved, a vacuum may be applied to an exposed end of the vascular pattern to extract the ink.

Advantageously, the tissue constructs may be designed to support the attachment and proliferation of endothelial cells, which line vascular channels providing a barrier to fluid diffusion, while simultaneously facilitating homeostatic functions and helping establish vascular niches specific to the various tissues. To promote endothelialization, in some embodiments the sacrificial filament(s) comprising the fugitive ink may further include a plurality of endothelial cells or other viable cells. The cells may be deposited along with the sacrificial filament and may remain in the vascular channels after removal of the fugitive ink, as illustrated in FIGS. 16A-16C. Direct cellularization of the channels can be achieved if the cells adsorb to the channel walls after liquidation of the fugitive ink. This approach may allow one to incorporate viable cells into highly tortuous networks or small channels that may be difficult to infill using direct injection due to an increased resistance to flow. An exemplary printed tissue construct including a channel formed by evacuation of a fugitive ink comprising endothelial cells and Pluronic F127 is shown in FIGS. 16D-16G, and is further described in the Examples. In another example, epithelial cells may be delivered in a fugitive ink and used to create tubular epithelial tissues present in the mammary gland, kidney or liver.

In addition to or as an alternative to depositing endothelial and/or other viable cells with the fugitive ink, endothelialization may be effected by injecting a suspension of viable cells (e.g., endothelial cells) into the vascular channels after removing the fugitive ink. Using one or both of these approaches, an endothelial layer having up to 100% confluency may be formed lining the wall of one or more of the vascular channels, where 100% confluency means that the wall is completely covered by endothelial cells. Each endothelial layer formed in the network of vascular channels may have a confluency of at least about 80%, at least about 90%, at least about 95%, at least about 98%, at least about 99%, or 100%, so that the vascular channels may function as actual blood vessels. As described in the Examples below, it has been shown that representative hierarchical bifurcating networks may be successfully injected with a human umbilical vein endothelial cell (HUVEC) suspension followed by gentle rocking (see FIG. 7J). After 48 h, these cells retained greater than 95% viability and assembled into a nearly confluent layer, as determined by live/dead staining coupled with confocal imaging within a representative, bifurcated microchannel.

Multiple types of cells may be injected into the vascular channels. In vivo, every blood vessel having a diameter larger than a capillary contains an outer fibrous tissue layer, a smooth muscle layer, and an inner layer of endothelial cells. One or more other types of cells, such as fibroblasts, may be injected into the vascular channels along with the endothelial cells after removing the fugitive ink. As described in the Examples below, the vascular channels may be co-seeded with fibroblasts and HUVECs, two cell types which may self-assemble into stromal and endothelial layers, respectively, mimicking the anatomy of native blood vessels.

It is also contemplated that the same or a different fugitive ink may be deposited as a sacrificial filament and removed as described above to form channels, ducts and/or compartments in addition to or in lieu of the vascular channels within the tissue construct. In other words, one or more additional sacrificial filaments may be deposited to form a functional channel pattern on the substrate, either in addition to or in lieu of the vascular pattern. This is shown schematically in FIG. 17A.

Figure 17A:
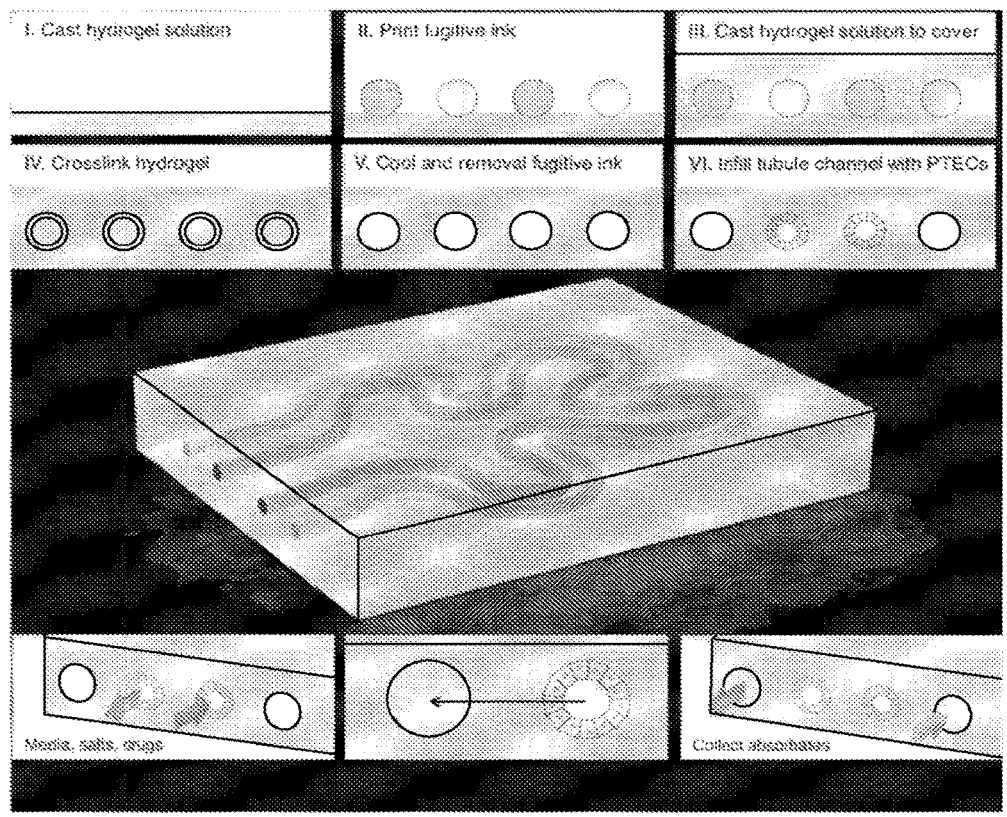
FIG. 17A illustrates the creation of one or more functional channels in an extracellular matrix composition to form a functional channel network in a tissue construct (specifically, in this example, an epithelial tissue construct). The steps include deposition of one or more sacrificial filaments comprising a fugitive ink (which may be a cell-laden fugitive ink) to form a functional channel pattern, at least partial encapsulation of the channel pattern with an extracellular matrix composition, removal of the fugitive ink to form the functional channels, and an optional seeding approach for lining the functional channels with epithelial cells.

Each additional sacrificial filament may comprise a second fugitive ink, which is the same as or different from the fugitive ink used to define the vascular pattern (if the vascular pattern is present). After deposition, the functional channel pattern may be at least partially surrounded with the extracellular matrix composition (e.g., the hydrogel solution shown in step III of FIG. 17A), as described above in reference to the vascular pattern. It is also contemplated that the at least partial surrounding of the functional channel pattern with the extracellular matrix composition may occur during deposition of the one or more sacrificial filaments, such that the one or more functional channel patterns are simultaneously formed and embedded in the extracellular matrix composition. When the forming and embedding of the functional channel patterns occurs simultaneously, the substrate onto which deposition occurs may be considered to be the container that holds the extracellular matrix composition or the extracellular matrix composition itself. The second fugitive ink may then be removed, as illustrated in step V of FIG. 17A and as described above in reference to the vascular channels, to create one or more functional channels in the extracellular matrix composition. Thus, a functional channel network may be formed in the tissue construct, which in this example is an epithelial tissue construct, as shown in FIGS. 17A (center) and 17B. One or more types of viable cells (e.g., epithelial cells) may be deposited with the additional sacrificial filaments, and at least a portion of the viable cells may remain in the one or more functional channels after removal of the second fugitive ink. Also or alternatively, after removing the second fugitive ink, a suspension of viable cells (e.g., epithelial cells) may be injected into the functional channels, as shown in step VI of FIG. 17A.

The functional channels may define tubular tissues or tissue components. Examples of tubular structures that can be formed via 3D printing and epithelialization include, but are not limited to, a nephron (of the kidney), intestine, milk duct, urethra, and lymph. Such a printed epithelial tissue construct may comprise one or more functional channels comprising an epithelial layer thereon, and an extracellular matrix composition may at least partially surround the one or more functional channels, as illustrated in FIGS. 17A (center) and 17B. A stromal layer may also be present on the epithelial layer. The printed epithelial tissue construct may further comprise one or more tissue patterns, each comprising a plurality of viable cells of one or more predetermined cell types, in the extracellular matrix composition, as set forth above. The viable cells and the one or more predetermined cell types may comprise epithelial cells and/or another cell type described previously. The printed epithelial tissue construct may further comprise a network of vascular channels in the extracellular matrix composition, also as described above.

For example, a network of vessels (channels) of the lymphatic system may be created using sacrificial filaments comprising a fugitive ink. In another example, compartments of any desired geometry may be embedded within the tissue construct by depositing a predetermined arrangement of sacrificial filaments. Such embedded compartments may be used for containing growth factors, additional cells and/or supplemental scaffold materials that may in some embodiments be deposited with the sacrificial filaments to direct cell behavior, differentiation, function, movement and/or growth.

Figure 17B:
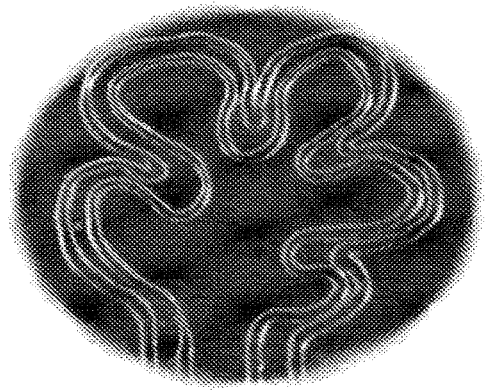

A printed epithelial tissue construct comprising a functional channel that is subsequently seeded with epithelial cells (epithelialization) is shown in FIGS. 17A-17F. Referring to FIGS. 17A-17B, the printed tissue construct is a proximal convoluted tubule, a portion of the nephron. It can be printed in a simple or convoluted shape and seeded with epithelial cells, which thrive and circumscribe the functional channels, as shown in FIGS. 17C-17F. The cells employed are human renal proximal tubule cells (PTEC); however, this approach may be applied to any of a number of types of epithelial tissue. For example, in vitro models may be fabricated for tissue-specific disease and toxicity studies. This type of functional human tissue mimic can be used as a building block for the growth of larger organs or for high throughput drug toxicity and screening.

Examples

Fugitive Ink

Referring to FIG. 6A, highly concentrated (40 wt. %) Pluronic F127A, which exhibits a strong shear-thinning response when the applied shear stress exceeds the shear yield stress ($\tau_y$) (e.g., during printing), as well as a plateau shear elastic modulus (G') that exceeds the shear viscous modulus (G") when the applied shear stress is below $\tau_y$ (e.g., after printing), is selected as the fugitive ink for an exemplary system. The fugitive ink elasticity is found to be about $2 \times 10^4$ Pa at 22° C., as shown in FIG. 6B. Below the CMT (about 4° C.), the ink liquefies and its elasticity decreases by several orders of magnitude, thereby facilitating its removal from the tissue construct.

As described above, the sacrificial filaments formed from the fugitive ink may include one or more additional cells, growth factors, drugs, etc. For example, endothelial, epithelial and/or other cells may be dispersed within the fugitive ink and deposited with the sacrificial filaments. When the fugitive ink is removed to form the vascular (or other) channels, the cells may remain, lining walls of the channels.

This approach is demonstrated with a highly concentrated endothelial cell-laden fugitive (pluronic) ink ($1 \times 10^7$ cells/ml). The fugitive ink is deposited and encapsulated with an extracellular matrix composition. Upon removal of the fugitive ink to form vascular channels, the endothelial cells remain affixed to walls of the channels, as shown schematically in FIGS. 16A-16C and experimentally in FIGS. 16D-16G. FIG. 16G shows a simple channel created using this approach that has been perfused for over 24 hours. The endothelial cells appear to line the channel and look qualitatively similar to those created using a conventional seeding approach. This technique provides an alternative to seeding existing vascular channels with endothelial cells, particularly in the case of highly branched vascular networks where cells may clog and inhibit flow, leading to non-uniform seeding.

Extracellular Matrix Composition and Material

As set forth above, an interpenetrating polymer network based on gelatin and fibrin has been developed that mimics natural ECM, and which may be used for the extracellular matrix composition and/or the extracellular matrix material of the tissue construct.

FIGS. 13A-13D show fabrication of a gelatin-fibrin interpenetrating polymer network, or gelatin-fibrin matrix. First, the gel precursors are first mixed together. Polymerizing fibrinogen via the enzyme thrombin forms a fibrin gel or network. This phase provides initial mechanical strength and rigidity, as indicated by an increase in shear elastic modulus. The second phase (gelatin) is then formed around the fibrin gel, and the two phases are slowly crosslinked together via transglutaminase (TG). FIGS. 13E and 13F show shear modulus versus time (G' and G") and a stress-strain curve for the gelatin-fibrin interpentrating polymer network.

Figure 14:
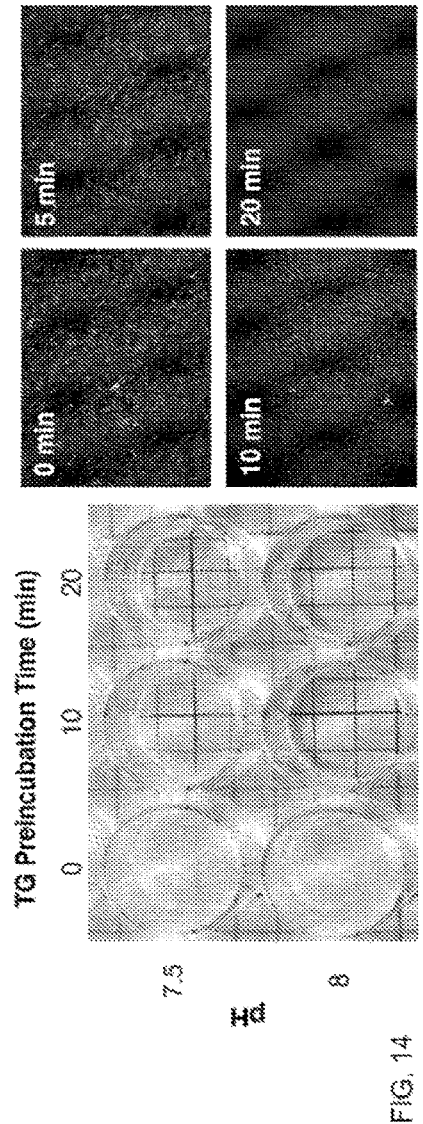
FIG. 14 illustrates the influence of TG incubation time on the optical properties of the fibrin-gelatin interpenetrating polymer network. Transparency is determined by the final pore architecture of the fibrin gel, which is visualized using a rhodamine tagged fibrinogen and confocal microscopy.

TG is a naturally occurring enzymatic protein crosslinker with myriad biological functions; for example, it may be up-regulated during wound healing in vivo. By varying TG incubation time, the optical properties (e.g., transparency) of the fibrin gel can be tailored. The transparency is dictated by the final pore architecture of the fibrin gel, which is visualized using a rhodamine-tagged fibrinogen and confocal microscopy. It is also of interest to determine if TG and gelatin disrupt natural fibrin polymerization. Confocal microscopy images reveal that the fibrillar nature of fibrin is preserved and can be precisely tuned by varying different processing conditions, such as incubation time, as illustrated in FIG. 14. A longer fibrin-TG incubation time leads to a more dense fibrillar network and, subsequently, higher optical transparency.

Besides fabrication considerations, cell material-interactions play an important role in materials selection. The gelatin-fibrin matrix has been shown to be compatible with many different cell types, including fibroblasts (connective tissue), smooth muscle cells, endothelial cells, and renal proximal tubule cells (epithelial). The adhesivity of the gelatin-fibrin matrix has been quantified by comparing the projected area of cells on various substrates. The gelatin-fibrin matrix outperformed all other materials including native fibrin, tissue culture polystyrene (TOPS), and gelatin methacrylate (GelMa). FIGS. 13G-13I show various cells essential for creating blood vessels—fibroblasts, endothelial cells, and smooth muscle cells—on an exemplary gelatin-fibrin matrix surface. To highlight the diversity of the adhesivity, tissue-specific epithelial cells were grown on the surface, as illustrated in FIG. 13J.

In a second example, gelatin methacrylate (GelMA), which is biocompatible, easily processed and inexpensive, is selected for use as both the extracellular matrix material for the cell-laden formulation and as the extracellular matrix composition for the encapsulation step. GelMA is denatured collagen that is modified with photopolymerizable methacrylate (MA) groups, which allows the matrix to be covalently cross-linked by UV light after printing. Physical gelation arises from the assembly of intermolecular triple helices that possess a structure similar to collagen, as illustrated in FIG. 6C. By varying the concentration, degree of methacrylation, and temperature, the shear yield stress and elastic modulus of aqueous GelMA systems can be systematically tuned.

The extracellular matrix composition is produced by dissolving 15 wt. % GelMA in cell culture media. Above approximately 25° C., the composition is a low viscosity fluid with a G' value below $10^{-1}$ Pa. Upon cooling below 25° C., the composition undergoes gelation, yielding a clear, viscoelastic extracellular matrix material. The elasticity of the extracellular matrix composition increases with decreasing temperature, with G' values of about $10^3$ Pa and $2\times10^4$ Pa observed at 22° C. and 2° C. (FIG. 6D), which correspond to typical conditions for printing and fugitive ink removal, respectively.

The same aqueous GelMA composition is used to create cell-laden inks that contain viable cells for printing. Prior studies have shown that cells adhere, remodel, and migrate through GelMA due to the presence of integrin-binding motifs and matrix metal-proteinase sensitive groups. It is found that the incorporation of a moderate concentration, e.g., $2\times10^6$ cells/mL, of 10T½ fibroblast cells into the 15 wt. % GelMA ink (FIGS. 6E and 6F) does not significantly alter the temperature at which gelation ensues or the elasticity of the composition over the temperature range of interest, e.g., 2° C. to 40° C. Hence, both pure and cell-laden GelMA inks can be printed and further processed, as needed, in the same manner.

The differences in thermally reversible gelation observed for the fugitive Pluronic F127, pure GelMA, and cell-laden GelMA inks give rise to three distinct processing windows. Between approximately 4° C. and 25° C., each ink is stiff and exhibits a solid-like response, where G'>G". At T≥25° C., the Pluronic F127 fugitive ink is stiff and solid-like (G'>G"), while the pure and cell-laden GelMA inks are liquids that flow readily. Below about 4° C., the Pluronic F127 fugitive ink is a liquid that flows readily, while the pure and cell-laden GelMA inks are stiff and solid-like (G'>G").

Printing of Vascular Patterns

Figures 7A, 7B, 7C, 7D, 7E, 7F, 7G, 7H, 7I, 7J, 7K:
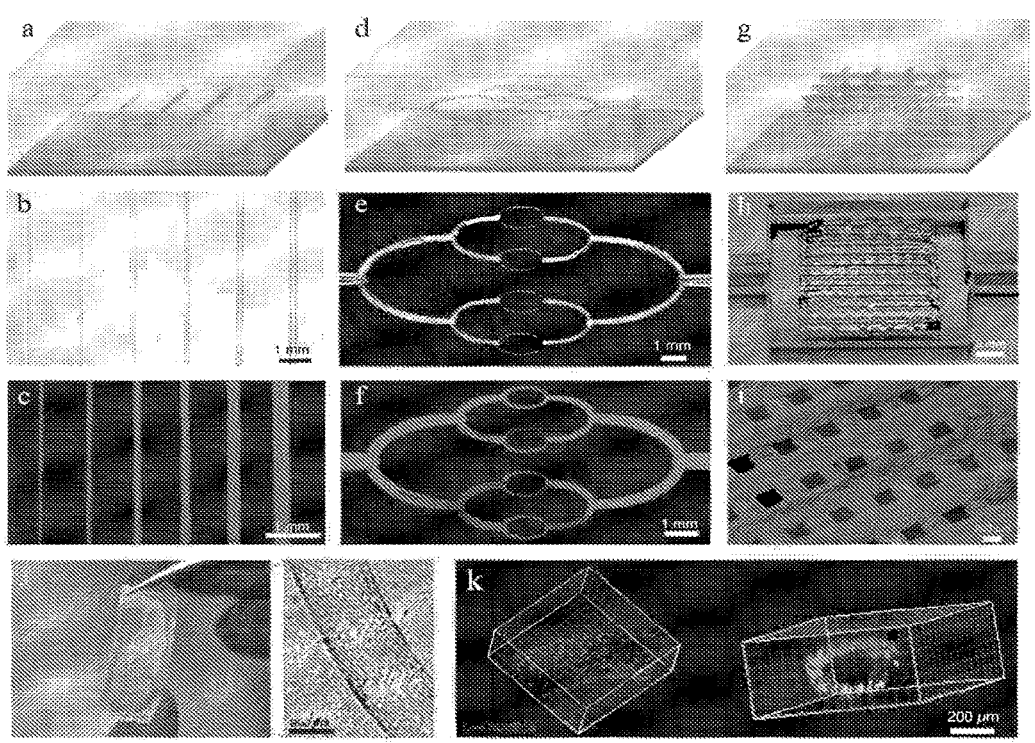
FIGS. 7A and 7B show 1D channels formed in GelMA, where diameters range from 115 µm to 500 µm.
FIG. 7C shows the channels perfused with a water-soluble fluorescent dye for visualization.
FIGS. 7D-7E show a 2D hierarchical branching network with curvilinear filaments printed using a single 30 µm glass capillary.
FIG. 7F shows the structure perfused with red fluorescent dye for visualization.
FIGS. 7G-7I show a highly periodic 3D lattice printed from sacrificial filaments to create a 3D vascular pattern that can be perfused after evacuation of the fugitive ink.
FIG. 7J shows an optical image of representative microchannel within a 2D vascular network perfused with a HUVEC suspension.
FIG. 7K shows a confocal image of the microchannel shown in FIG. 7J with live HUVEC cells lining the microchannel walls.

The complimentary thermal behavior described above for the Pluronic F127-GelMA system is exploited to print representative vascular patterns comprising a plurality of sacrificial filaments which are then encapsulated in an acellular extracellular matrix composition (pure GelMA). FIGS. 7A-7K illustrate the formation of 1D, 2D and 3D vascular networks and endothelialization of the channels, with schematic views and corresponding optical images of each vascular network design. After removing the fugitive ink, each vascular network is perfused with a fluorescent red dye to aid in visualization (FIGS. 7C, 7F and 7I). Within each tissue construct, the diameter of the sacrificial filaments can be altered as desired by modifying the printing pressure, speed, and/or nozzle height. For example, 1-D microchannel arrays with diameters increasing from 45 μm to 500 μm are printed using a single 30 μm nozzle simply by increasing the printing pressure and nozzle height in a stepwise fashion between each printed feature (FIGS. 7A-7B).

Figures 8A, 8B:
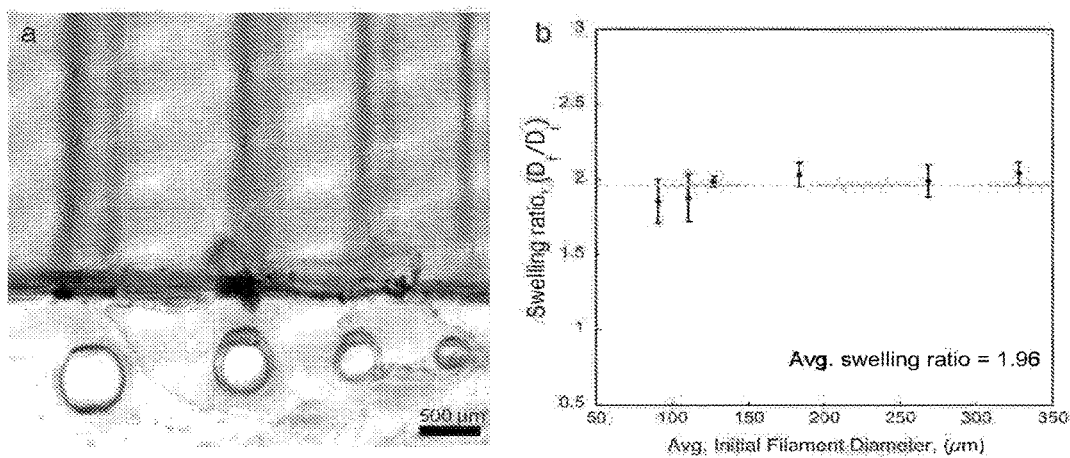
FIG. 8A shows representative cross-sections of various channel diameters created by depositing sacrificial filaments and removing the fugitive ink.
FIG. 8B is a plot showing the swelling ratio ($D_{final}/D_{initial}$) of various printed sacrificial filaments comprising Pluronic F127. Each data point is an average of six samples, each deposited at a fixed speed, pressure, and nozzle height (z axis). The diameters are measured directly after printing and again after evacuation via top-down optical microscopy.
Figures 9A, 9B, 9C, 9D:
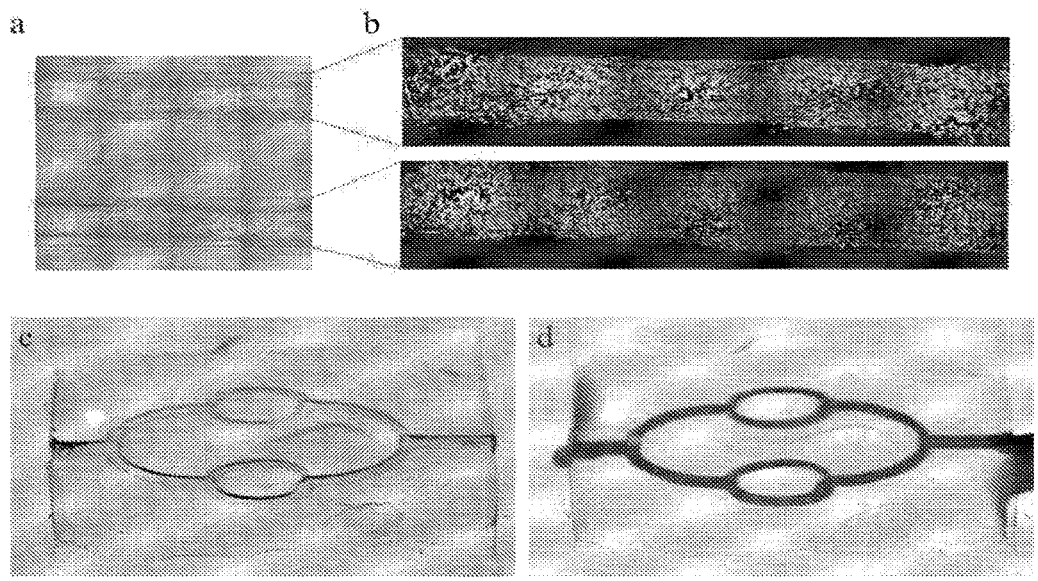
FIGS. 9A-9B show that endothelialized vascular channels can be created in fibrin gel, as shown.
FIGS. 9C and 9D show before and after photographs of animal blood infiltration in a fabricated bifurcating vascular network.

After photopolymerizing the GelMA matrix, the fugitive ink is removed by cooling the printed constructs below 4° C., yielding open 1-D microchannels. Representative cross-sectional images of these 1-D channels, shown in FIG. 8A, reveal that their final diameters range from about 100 μm to about 1 mm. Since the GelMA ink has a higher water content than the fugitive ink, the printed vascular features may swell as water diffuses into the fugitive ink (Pluronic F127) from the surrounding matrix. Indeed, the diameters nearly double in size, with a swelling ratio that is independent of initial microchannel diameter (FIG. 8B) for this material system.

The 2-D vascular network design mimics the hierarchical, bifurcating motifs found in biological systems, large channels bifurcate to form smaller channels that maximize efficient blood flow, nutrient transport, and waste removal while minimizing the metabolic cost. These 2D hierarchical vascular networks are printed using a single nozzle of 30 microns (e.g., FIGS. 7E and 7F). The as-printed, largest channels (650 μm in diameter) provide a single inlet and outlet for perfusion, while the smallest channels (45 μm) in diameter) reduce the characteristic diffusion distance between adjacent conduits. Finally, a 3D microvascular network design, which is shown in FIGS. 7G, 7H and 7I and includes a 3D periodic array of uniform microchannels, is printed. Because the embedded microchannels are interconnected in all three dimensions, the fugitive ink can be removed from the surrounding GelMA matrix quickly and with high fidelity.

Seeding of Vascular Channels

Multiple types of fluids may be flowed through embedded vascular networks to demonstrate their perfusable nature. For example, the 2D hierarchical bifurcating networks are injected with a human umbilical vein endothelial cell (HUVEC) suspension followed by gentle rocking. After 48 h, it is found that the cells retained greater than 95% viability and assembled into a nearly confluent layer, as determined by live/dead staining coupled with confocal imaging within a representative, bifurcated microchannel.

Figure 18A:
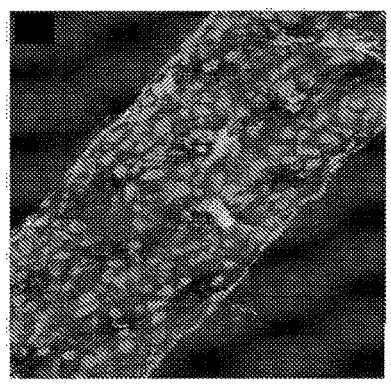
FIGS. 18A-18C highlight the initially uniform distribution of HUVECs (red) and HNDFs (green) at 3 days post-seeding.
Figure 18B:
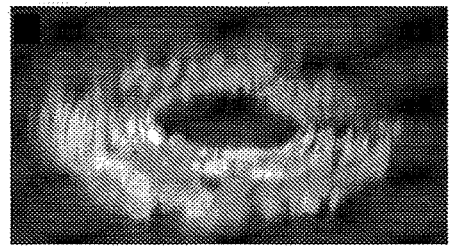
Figure 18C:
Figure 18D:
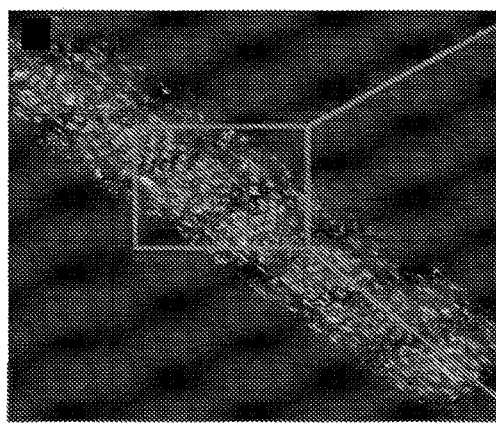
FIGS. 18D-18E shows the same channel after eight days, at which time the channel comprises a distinct outer stromal (HNDF) layer and a confluent endothelial (HUVEC) layer.
Figure 18E:
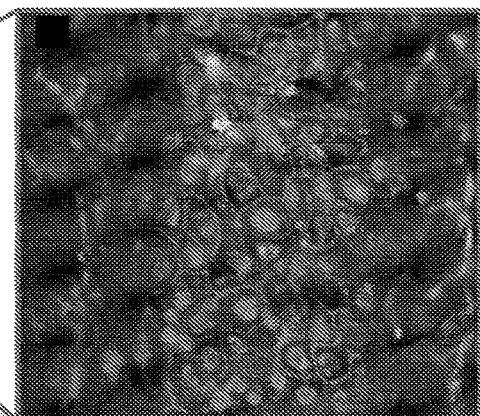

The vascular channels may be seeded with multiple cell types, such as fibroblasts or smooth muscle cells in addition to HUVECs. Here, fibroblasts are co-seeded with HUVECs. It is found that, after about one week of perfusion culture, uniformly co-seeded endothelial cells and fibroblasts self assemble into two distinct layers of outer enveloping stroma (human dermal fibroblasts; HNDFs) and confluent inner endothelium (HUVECs). FIGS. 18A-18C highlight the initially uniform distribution of HUVECs (red) and HNDFs (green) at 3 days post-seeding. FIGS. 18D-18E shows the same channel after eight days, at which time the channel comprises a distinct outer stromal (HNDF) layer and a confluent endothelial (HUVEC) layer. The confluent endothelium is visualized using immunohistochemistry to stain for vascular endothelial cadherin (VE-Cad), an endothelial-specific junction protein expressed when cells form confluent networks (shown in magenta).

To further promote the attachment and proliferation of the endothelial cells along the fabricated channel walls, the interior of the walls may be coated by perfusing a fibronectin solution through the channels prior to introducing the HUVEC suspension, as shown in FIGS. 9A-9D. Also, when animal blood is directly injected into the inlet of the 2-D vascular network it rapidly flows through the entire network to outlet. These initial demonstrations illustrate the potential to create perfusable vasculature of nearly any arbitrary design.

Printing of Cell-Laden Filaments Including More than One Cell Type

The printing of cell co-culture inks that allow the delivery of two or more cell types within a single ink filament is demonstrated. It is observed that a cell-laden ink including, in this example, a dispersion of HNDFs and HUVECs in a gelatin-fibrin matrix material, leads to spontaneous neovasculature formation in the printed filament, as evidenced in FIGS. 20A-20C. This is not observed in printed filaments based on a monoculture of HUVECs. This approach suggests cell-laden filaments comprising more than one cell type, including tissue-specific cell types (e.g., hepatocytes, islets, podocytes, neurons, etc.) or stem cells (e.g., iPSCs, MSCs, etc), may be used to achieve desired heterogeneity and also to enhance function.

Printing of Fugitive Ink onto a Cell-Laden Matrix

As in the previous example, HNDFs and HUVECs are dispersed within an extracellular matrix composition (specifically, a gelatin-fibrin matrix material) to form a cell-laden matrix. A fugitive ink is printed directly onto the cell-laden matrix and then encapsulated by the gelatin-fibrin matrix material. The fugitive ink is evacuated to form vascular channels, and the vascular channels are seeded with HUVECs. Over time, it is found that the HUVECs assemble into capillary structures within the printed cell-laden filament. FIGS. 19A-19D show that the endothelial cells become attached to the vascular channels and form confluent layers, and FIGS. 19E-19F show evidence of angiogenic sprouting of small capillaries from the confluent blood vessels indicating that the process is conducive to cellular remodeling and higher-level biological processes.

Two effects are hypothesized to contribute to this observed behavior. First, fibroblasts have been shown numerous times to be pro-angiogenic support cells in vitro through specific chemical cues such as fibroblast growth factor (FGF), often leading to neovascularization processes. Additionally, the concentrated population of proliferative cells within the matrix has extensive metabolic requirements that are likely not met by diffusion alone. It is widely accepted that cells that are not within a few 100 microns of blood vessel will become oxygen stressed and eventually necrotic. In vivo, the recruitment of host vasculature into avascular structures to prevent necrosis has been observed.

Printing of Tissue Constructs Including Interpenetrating Vasculature

To demonstrate the fabrication of tissue constructs replete with blood vessels, multiple types of cells, and an extracellular matrix composition, 3D heterogeneous structures of varying design are printed.

The first structure is composed of semi-woven features printed in and out of plane (FIGS. 10A-10G). This four-layer tissue construct includes two tissue patterns each comprising a different cell type and a vascular pattern formed from sacrificial filaments comprising a fugitive ink. The tissue construct is produced in a layer by layer build sequence by printing four inks: PDMS, fugitive Pluronic F127 and two different cell-laden GelMA inks, followed by depositing pure GelMA ink at 37° C. to fully encapsulate the printed features, and finally photopolymerization to cross-link the GelMA matrix. This 3D architecture was conceived and fabricated to demonstrate the printing capabilities and also facilitate confocal imaging through the entire 4-layer, printed construct.

Figures 10A, 10B, 10C, 10D, 10E, 10F, 10G:
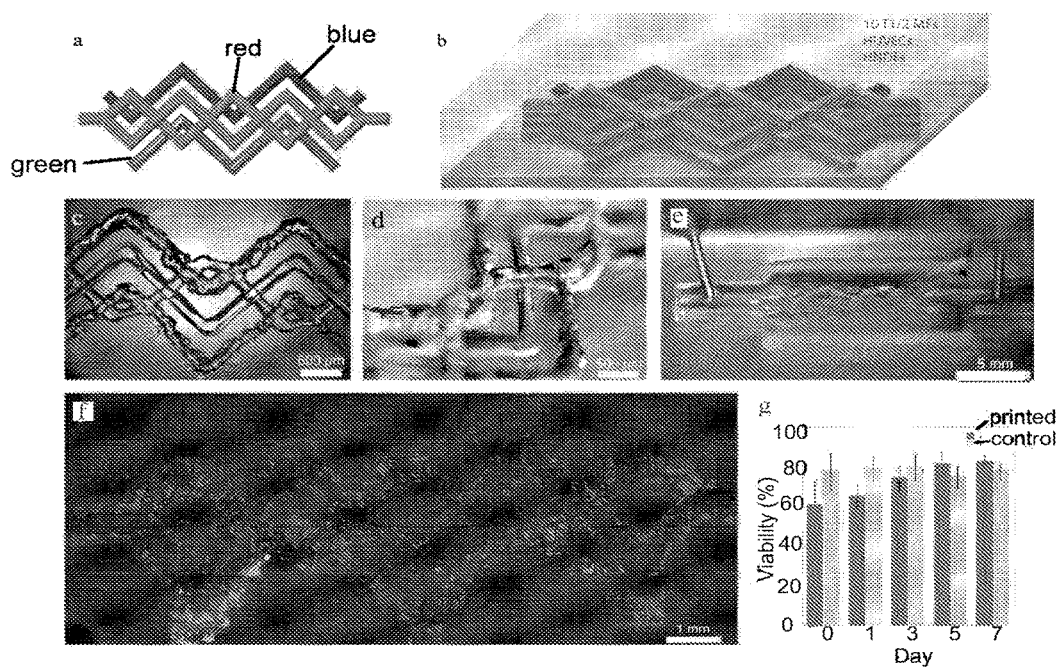
FIG. 10A provides a top-down view of a final 3D printed heterogeneous tissue constructs structure that is printed from four separate inks.
FIG. 10B provides an angled view of the complex toolpath used to create the tissue construct shown in FIG. 10A, where the green filaments comprise GFP HNDF-laden GelMA, the blue filaments comprise 10T½ fibroblast-laden GelMA, and the red filaments comprise the Pluronic ink that may be endothelialized with RFP HUVECs. The gray shaded region corresponds to pure GelMA matrix that encapsulates the 3D printed construct.
FIG. 10C is a bright field microscopy image overlaid with the green fluorescent channel of the structure of FIG. 10A directly after printing.
FIG. 10D is a photograph illustrating the spanning and out-of-plane nature of the printed structure.
FIG. 10E shows a demonstration of the fugitive ink evacuation process.
FIG. 10F provides a composite image of the three fluorescent channels: 10T½ fibroblasts (blue), HNDFs (green), HUVECs (red) from the structure of FIG. 10A.
FIG. 10G shows cell-viability assay results of printed 10T½ fibroblasts compared with a non-printed control.
Figures 11A, 11B, 11C:
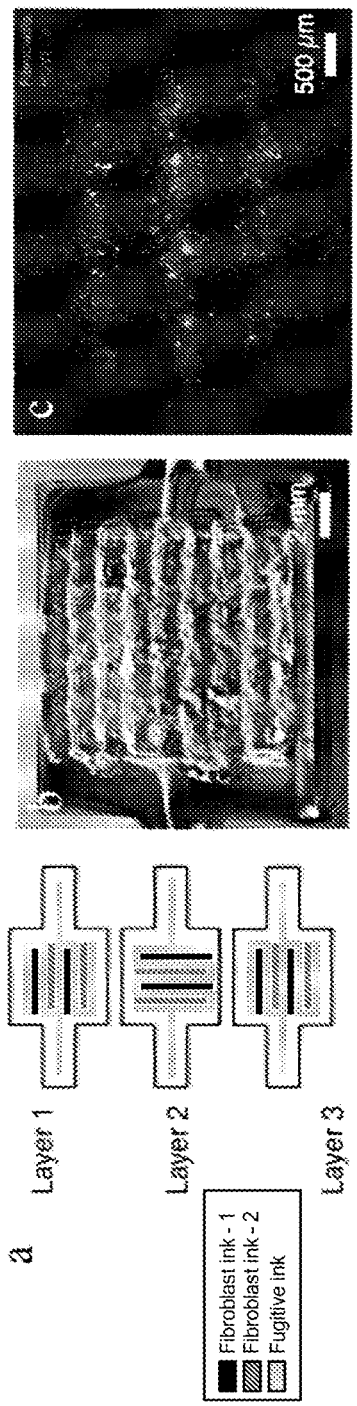
FIG. 11A shows a schematic of a three-layered structure containing multiple cell-laden filaments and sacrificial filaments comprising a fugitive ink.
FIG. 11B shows a photograph of the evacuated microstructure before endothelialization.
FIG. 11C shows an epifluorescent image of GFP HNDFs (green) and RFP HUVECs (red) after two days in culture.

As indicated previously, the PDMS ink is first printed in the form of a high-aspect ratio border that surrounds each tissue construct and serves as a mold for the pure GelMA ink used for the encapsulation step. The fugitive ink and both cell-laden GelMA inks, which contain either green fluorescent protein expressing human neonatal dermal fibroblasts (HNDFs) or non-fluorescent 10T½s, an established mouse fibroblast line, are co-printed at concentrations of $2 \times 10^6$ cells/mL through 200 µm nozzles in a predefined sequential process. FIG. 10C shows an image of the 3D structure directly after printing. Only the green fluorescent channel is overlaid onto the bright field image so that the printed cell channel can be easily visualized. After fabrication, the fugitive ink is liquefied and removed from the 3D construct. The evacuation procedure involves placing empty syringe tips into the inlet and outlet microchannels and then suctioning out the entire vascular network under a modest vacuum. The removal process is rapid and yields a high fidelity, interpenetrating vasculature, which is then endothelialized as described above.

Characterization of the Tissue Constructs

Using microscopy, the locations of the three cell types that are independently stained (green-GFP HNDFs, blue-10T½, and red-HUVECs) are identified. The semi-woven nature of this engineered tissue construct is clearly visible in the schematics and images shown in FIGS. 10B-10D. Using confocal laser scanning microscopy, it is possible to fully interrogate this 3D tissue construct and determine the precise locations of each cell. Confocal microscopy images of the 3-D printed structure in XY, XZ, and YZ after 2 days of culture are shown in FIG. 10G. To demonstrate the versatility of this approach, other 3D tissue construct were also designed and printed. Although it is difficult to obtain confocal images due the dense, interpenetrating nature of the cell-laden filaments, both the green fluorescent protein expressing HNDFs in GelMA and the red-HUVECs that line the 3-D vasculature network are visible.

Investigation of Cell Viability

As a final step, the viability of the printed 10T½ fibroblast cells over the course of one week was investigated. At Day 0, the cell viability was 61%; however, it increased to 82% after 7 days. While there is lower initial cell viability compared with the control (78% on Day 0), the printed cells do proliferate and spread over time leading to similar levels of viability after 1 week in culture. The decreased initial viability could arise from the shear or extensional stress experienced by the cells during the printing process. Applied pressure, nozzle diameter, cell type, and environmental conditions may affect cell viability after printing. Another critical parameter is the total build time required to print the desired engineered tissue construct. There may be a maximum time over which the cell-laden inks can be stored in the ink reservoir prior to being harmed. However, implementation of multinozzle print heads that were reported previously (J. A. Lewis et al., "Multinozzle Deposition System for Direct Write Applications," International Patent Application No. PCT/US2012/044794, filed Jun. 29, 2012, which is hereby incorporated by reference) for high-throughput, multimaterial printing, may reduce the characteristic build times by two orders of magnitude in comparison with single nozzle printing. For example, printing an engineered tissue construct with a volume of 1000 cm³, comparable to a typical adult human liver, could require approximately 72 h using a single 200 μm nozzle at typical printing speeds. However, implementation of a 64-multinozzle array may reduce the respective build time to about 1 h.

A new approach has been developed and described in the present disclosure for creating vascularized, heterogeneous tissue constructs on demand via 3D bioprinting. This highly scalable platform enables the fabrication of engineered tissue constructs in which vasculature, multiple cell types and optionally other functional chemical substances, such as drugs, toxins, proteins and/or hormones, are programmably placed at desired locations within an extracellular matrix. This technique may lead to the rapid manufacturing of functional 3D tissues and organs needed for transplant.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of printing a tissue construct, comprising:
   depositing one or more cell-laden filaments each comprising a plurality of viable cells on a substrate to form one or more tissue patterns, each of the tissue patterns comprising one or more predetermined cell types;
   depositing one or more sacrificial filaments on the substrate to form a vascular channel pattern interpenetrating the one or more tissue patterns, each of the sacrificial filaments comprising a fugitive ink, wherein the fugitive ink comprises additional viable cells;
   at least partially surrounding the one or more tissue patterns and the vascular channel pattern with an extracellular matrix composition; and
   removing the fugitive ink to create an interconnected vascular channel network interpenetrating the one or more tissue patterns in the extracellular matrix composition, wherein at least a portion of the additional viable cells remains in the interconnected vascular channel network after removal of the fugitive ink.

2. The method of claim 1, wherein the additional viable cells are at least one of endothelial cells, smooth muscle cells, or connective tissue cells.

3. The method of claim 1, wherein each of the one or more cell-laden filaments further comprise an extracellular matrix material comprising one or more of gelatin, fibrin, and gelatin methacrylate.

4. The method of claim 1, wherein at least one of the one or more cell-laden filaments further comprises one or more functional chemical substances selected from the group consisting of: drugs, small molecules, toxins, proteins, and hormones.

5. The method of claim 1, wherein each of the one or more cell-laden filaments and each of the one or more sacrificial filaments are extruded from a nozzle at room temperature before being deposited on the substrate.

6. The method of claim 1, wherein removing the fugitive ink comprises cooling the one or more sacrificial filaments.

7. The method of claim 1, further comprising at least one of the following steps:
   after removing the fugitive ink, injecting a suspension of endothelial cells into the interconnected vascular channel network; or
   depositing one or more structural filaments layer by layer on the substrate to form a mold prior to at least partially surrounding the one or more tissue patterns and the vascular channel pattern with the extracellular matrix composition.

8. The method of claim 7, wherein the mold comprises flow channels in fluid communication with the vascular channels for perfusion thereof after removal of the fugitive ink.

9. The method of claim 7, further comprising:
   depositing one or more additional sacrificial filaments on the substrate to form a second vascular channel pattern, each of the additional sacrificial filaments comprising a second fugitive ink;
   at least partially surrounding the second vascular channel pattern with the extracellular matrix composition, and
   removing the second fugitive ink to create a second interconnected vascular channel network in the extracellular matrix composition,
   wherein, optionally, the second fugitive ink comprises additional viable cells, and wherein at least a portion of the additional viable cells remain in the second interconnected vascular channel network after removal of the second fugitive ink.

10. The method of claim 9, further comprising, after removing the second fugitive ink, injecting a suspension of additional viable cells into the second interconnected vascular channel network, wherein the additional viable cells comprise epithelial cells.

11. The method of claim 9, wherein the at least partial surrounding of the one or more tissue patterns and the vascular channel pattern with the extracellular matrix composition occurs during deposition of the one or more cell-laden filaments and the one or more sacrificial filaments, the one or more tissue patterns and the vascular channel pattern thereby being formed and embedded simultaneously in the extracellular matrix composition.

* * * * *